United States Patent
Olivo et al.

(10) Patent No.: US 9,915,670 B2
(45) Date of Patent: Mar. 13, 2018

(54) METHOD OF DETECTING HYDROGEN PEROXIDE

(71) Applicants: Nanyang Technological University, Singapore (SG); Agency for Science, Technology and Research, Singapore (SG)

(72) Inventors: Malini Olivo, Singapore (SG); Kien Voon Kong, Singapore (SG); Weng Kee Leong, Singapore (SG)

(73) Assignees: Nanyang Technological University, Singapore (SG); Agency for Science, Technology, and Research, Singapore (SG)

( * ) Notice: Subject to any disclaimer, the term of this patent is extended or adjusted under 35 U.S.C. 154(b) by 0 days.

(21) Appl. No.: 15/022,362

(22) PCT Filed: Sep. 16, 2014

(86) PCT No.: PCT/SG2014/000437
§ 371 (c)(1),
(2) Date: Mar. 16, 2016

(87) PCT Pub. No.: WO2015/038077
PCT Pub. Date: Mar. 19, 2015

(65) Prior Publication Data
US 2016/0231337 A1 Aug. 11, 2016

(30) Foreign Application Priority Data
Sep. 16, 2013 (SG) .............................. 2013069612

(51) Int. Cl.
*C12Q 1/28* (2006.01)
*G01N 33/84* (2006.01)
(Continued)

(52) U.S. Cl.
CPC .............. *G01N 33/84* (2013.01); *B82Y 15/00* (2013.01); *C01G 55/008* (2013.01); *C12Q 1/26* (2013.01);
(Continued)

(58) Field of Classification Search
CPC ........................................................ C12Q 1/28
See application file for complete search history.

(56) References Cited

U.S. PATENT DOCUMENTS

| 6,129,831 A | 10/2000 | Temmerman et al. |
| 8,178,357 B2 | 5/2012 | Trogler et al. |

(Continued)

FOREIGN PATENT DOCUMENTS

| WO | WO 97/39344 | 10/1997 |
| WO | WO 99/53301 | 10/1999 |

(Continued)

OTHER PUBLICATIONS

Kong et al., "Metal carbonyl-gold nanoparticle conjugates for live-cell SERS imaging," Angewandte Chemie Int. Ed. 51(39):9796-9799), published on Sep. 3, 2012, Abstract.*

(Continued)

*Primary Examiner* — Rosanne Kosson
(74) *Attorney, Agent, or Firm* — Alston & Bird LLP

(57) ABSTRACT

A method of detecting one or more analytes comprising or consisting of hydrogen peroxide using surface enhanced Raman spectroscopy (SERS) is provided. The method includes providing a SERS-active substrate having at least one metal carbonyl cluster compound attached thereon; contacting one or more analytes with the SERS-active substrate; and detecting changes in surface enhanced Raman signal from the at least one metal carbonyl cluster compound as an indication of the presence of one or more analytes comprising or consisting of hydrogen peroxide.

20 Claims, 31 Drawing Sheets

(51) Int. Cl.
  B82Y 15/00     (2011.01)
  G01N 21/65     (2006.01)
  C01G 55/00     (2006.01)
  C12Q 1/26      (2006.01)
  C12Q 1/54      (2006.01)
  G01N 33/58     (2006.01)
(52) U.S. Cl.
  CPC .............. *C12Q 1/54* (2013.01); *G01N 21/658* (2013.01); *G01N 33/587* (2013.01); *G01N 2333/904* (2013.01)

(56) References Cited

U.S. PATENT DOCUMENTS

| 8,426,213 B2 | 4/2013 | Eckhardt et al. |
| 2012/0276651 A1 | 11/2012 | Kim et al. |
| 2013/0045497 A1 | 2/2013 | Klaubert et al. |

FOREIGN PATENT DOCUMENTS

| WO | WO 2007/007199 A2 | 1/2007 |
| WO | WO 2008/088357 A1 | 7/2008 |
| WO | WO 2009/017631 A3 | 2/2009 |
| WO | WO 2010/117938 A1 | 10/2010 |
| WO | WO 2011/053247 A1 | 5/2011 |
| WO | WO 2013/025885 A1 | 2/2013 |

OTHER PUBLICATIONS

Abalde-Cela, S. et al. "Loading of Exponentially Grown LBL Films with Silver Nanoparticles and Their Application to Generalized SERS Detection." Angew Chem Int Ed, 2009, 48, pp. 5326-5329.
Abo, M. et al. "Development of a Highly Sensitive Fluorescence Probe for Hydrogen Peroxide." Journal of the American Chemical Society, 2011, 133, pp. 10629-10637.
Albers, A.E. et al. "A FRET-Based Approach to Ratiometric Fluorescence Detection of Hydrogen Peroxide." Journal of the American Chemical Society, 2006, 128, pp. 9640-9641.
Alberto, R. et al. "Chemistry and Biological Activities of CO-Releasing Molecules (CORMs) and Transition Metal Complexes." Dalton Transactions, 2007, pp. 1651-1660.
Barhoumi, A. "Label-Free Detection of DNA Hybridization Using Surface Enhanced Raman Spectroscopy." Journal of the American Chemical Society, 2010, 132, pp. 12792-12793.
Barriet, D. et al. "4-Mercaptophenylboronic Acid SAMs on Gold: Comparison with SAMs Derived from Thiophenol, 4-Mercaptophenol, and 4-Mercaptobenzoic Acid." Langmuir : the ACS Journal of Surfaces and Colloids, 2007, 23, pp. 8866-8875.
Begum, N. et al. "Reactions of [($\mu$-H)Os$_3$(CO)$_8$-{Ph$_2$PCH$_2$P(Ph)C$_6$H$_4$}] and [Os$_3$(CO)$_{10}$($\mu$-H)Os$_3$(CO)$_8$ ($\mu$-dppm)($\mu$-$\eta$]$^1$-SN$_2$C$_3$H$_3$)]." Indian Journal of Chemistry, vol. 44A, Apr. 2005, pp. 723-728.
Bell, S.E.J. et al. "Surface-Enhanced Raman Spectroscopy (SERS) for Sub-Micromolar Detection of DNA/RNA Mononucleotides." Journal of the American Chemical Society, 2006, 128, pp. 15580-15581.
Boczkowski, J. et al. "CO-Metal Interaction: Vital Signaling From a Lethal Gas." Trends in Biochemical Sciences, 2006, 31, pp. 614-621.
Chang, M.C.Y. et al. "A Selective, Cell-Permeable Optical Probe for Hydrogen Peroxide in Living Cells." Journal of the American Chemical Society, 2004, 126, pp. 15392-15393.
Chen, Q. et al. "Raman Spectroscopy for Hydrogen Peroxide Scavenging Activity Assay Using Gold Nanoshell Precursor Nanocomposites as SERS Probes." Analytical Methods, 2011, 3, pp. 274-279.
Daniel, K.B. et al. "Readily Accessible Fluorescent Probes for Sensitive Biological Imaging of Hydrogen Peroxide." Chembiochem : a European Journal of Chemical Biology, 2013, 14, pp. 593-598.

Dasog, M. et al. "Understanding the Oxidative Stability of Gold Monolayer-Protected Clusters in the Presence Of Halide Ions under Ambient Conditions." The ACS Journal of Surfaces and Colloids, 2007, 23, pp. 3381-3387.
Dickinson, B.C. et al. "A Palette of Fluorescent Probes with Varying Emission Colors for Imaging Hydrogen Peroxide Signaling in Living Cells." Journal of the American Chemical Society, 2010, 132, pp. 5906-5915.
Dickinson, B.C. et al. "A Targetable Fluorescent Probe for Imaging Hydrogen Peroxide in the Mitochondria of Living Cells." Journal of the American Chemical Society, 2008, 130, pp. 9638-9639.
Fischer-Durand, N. et al. "Site-Specific Conjugation of Metal Carbonyl Dendrimer to Antibody and Its Use as Detection Reagent in Immunoassay." Analytical Biochemestry, 2010, 407, pp. 211-219.
Graham, D. "The Next Generation of Advanced Spectroscopy: Surface Enhanced Raman Scattering from Metal Nanoparticles." Angew Chem Int Ed, 2010, 49, pp. 9325-9327.
Groegel, D.B.M. et al. "A New Fluorescent. PET Probe for Hydrogen Peroxide and its Use in Enzymatic Assays for l-Lactate and d-Glucose." ChemBioChem : a European Journal of Chemical Biology, 2011, 12, pp. 2779-2785.
Gübitz, G. et al. "Immobilized Fluorophores in Dynamic Chemiluminescence Detection of Hydrogen Peroxide." Analytical Chemistry 1985, 57, pp. 2071-2074.
Haquette, P. et al. "Cysteine-Specific, Covalent Anchoring of Transition Organometallic Complexes to the Protein Papain from Carica Papaya." ChemBioChem: a European Journal of Chemical Biology, 2007, 8, pp. 224-231.
Hitomi, Y. et al. "Detection of Enzymatically Generated Hydrogen. Peroxide by Metal-Based Fluorescent Probe." Analytical Chemistry, ACS Publications, 2011, 83, pp. 9213-9216.
Hromadová, M. et al. "Electrochemical Microbead-Based Immunoassay Using an ($\eta^5$-Cyclopentadienyl)tricarbonylmanganese Redox Marker Bound to Bovine Serum Albumin." Langmuir: the ACS Journal of Surfaces and Colloids, 2006, 22, pp. 506-511.
Jin, R. "Nanoparticle Clusters Light Up in SERS." Angew Chem Int Ed, 2010, 49, pp. 2826-2829.
Johnson, T.R. et al. "Metal Carbonyls: A New Class of Pharmaceuticals." Angew Chem Int Ed, 2003, 42, pp. 3722-3729.
Karton-Lifshin, N. et al, "A Unique Paradigm for a Turn-On Near-Infrared Cyanine-Based Probe: Noninvasive Intravital Optical Imaging of Hydrogen Peroxide." Journal of the American Chemical Society, 2011, 133, pp. 10960-10965.
Kawasaki, T. et al. "Increased Fructose Concentrations in Blood and Urine in Patients with Diabetes." Diabetes Care, 2002, 25, pp. 353-357.
Kim, K. et al. "Effect of Organic Vapors and Potential-Dependent Raman Scattering of 2,6-Dimethylphenylisocyanide on Platinum Nanoaggregates." Physical Chemistry Chemical Physics, 2011, 13, pp. 5981-5986.
Kim, K. et al. "Effects of Polar Organic Vapors on Surface Potential of Au Nanoparticle Aggregates Probed by Surface-Enhanced Raman Scattering of 2,6-Dimethylphenylisocyanide." Chemical Communications, 2010, 46, pp. 3753-3755.
Kim, K. et al. "Organic Isocyanide-Adsorbed Gold Nanostructure: a SERS Sensory Device for Indirect Peak-Shift Detection of Volatile Organic Compounds," Analyst, 2012, 137, pp. 1930-1936.
Kim, K. et al. "pH Effect on Surface Potential of Polyelectrolytes-Capped Gold Nanoparticles Probed by Surface-Enhanced Raman Scattering." Langmuir : the ACS Journal of Surfaces and Colloids, 2010, 26, pp. 19163-19169.
Kim, K. et al. "Surface Potential of Au Nanoparticles Affected by Layer-by-Layer Deposition of Polyelectrolytes: A Surface-Enhanced Raman Scattering Study." Journal of Physical Chemistry C, 2010, 114, pp. 9917-9922.
Kiriakidou, K. et al. "Detection of a novel intermediate in the addition of thiols to osmium carbonyl clusters", Chem Commun., 1998, pp. 2721-2722.
Kneipp, K. et al. "Surface-Enhanced Raman Scattering in Local Optical Fields of Silver and Gold Nanoaggregates From Single-

(56) References Cited

OTHER PUBLICATIONS

Molecule Raman Spectroscopy to Ultrasensitive Probing in Live Cells." Accounts of Chemical Research, 2006, 39, pp. 443-450.
Kneipp, K. et al. "Surface-Enhanced Raman Spectroscopy in Single Living Cells Using Gold Nanoparticles." Applied Spectroscopy, 2002, 56, pp. 150-154.
Kneipp, K. et al. "Ultrasensitive Chemical Analysis by Raman Spectroscopy." Chemical Reviews, 1999, 99, pp. 2957-2975.
Kong, K.V. et al. "Bioimaging in the Mid-Infrared Using an Organometallic Carbonyl Tag." Bioconjugate Chemistry, 2007, 18, pp. 1370-1374.
Kong, K.V. et al. "Metal Carbonyl-Gold Nanoparticle Conjugatse for Live-Cell SERS Imaging." Angew Chem Int Ed, 2012, 51, pp. 9796-9799.
Kong, K.V. et al. "Osmium Carbonyl Clusters Containing Labile Ligands Hyperstabilize Microtubules." Chemical Research in Toxicology, 2009, 22, pp. 1116-1122.
Kong, K.V. et al. "Osmium Carbonyl Clusters: A New Class of Apoptosis Inducing Agents." ChemMedChem, 2008, 3, pp. 1269-1275.
Lal, S. et al. "Nano-optics From Sensing to Waveguiding." Nature Photonics, 2007, 1, pp. 641-648.
Li, G. et al. "Rapid Detection of Hydrogen Peroxide Based on Aggregation Induced Ratiometric Fluorescence Change." Organic Letters 2013, 15, pp. 924-927.
Liu, Y.A. et al. "Fluorescent Probes for the Detection of Hydrogen Peroxide in Biological Systems." Current Organic Chemistry, 2013, 17, pp. 654-669.
Lo, L-C. et al. "Development of Highly Selective and Sensitive Probes for Hydrogen Peroxide." Chemical Communications, 2003, pp. 2728-2729.
Luo, W. et al. "Self-Catalyzed, Self-Limiting Growth of Glucose Oxidase-Mimicking Gold Nanoparticles." ACS Nano, 2010, 4, pp. 7451-7458.
Lyandres et al. "Surface-Enhanced Raman Sensors for Metabolic Analytes." Biomedical Vibrational Spectroscopy, John Wiley & Sons, Inc., 2008, pp. 221-242.
Lyon, J.L. et al. "Picomolar Peroxide Detection Using a Chemically Activated Redox Mediator and Square Wave Voltammetry." Analytical Chemistry, 2006, 78, pp. 8518-8525.
Drábková, M. et al. "Combined Exposure to Hydrogen Peroxide and Light—Selective Effects on Cyanobacteria, Green Algae, and Diatoms." Environmental Science & Technology 2007, 41, pp. 309-314.
Mann, B.E. et al. "CO and NO In Medicine." Chem Commun (Camb), 2007, pp. 4197-4208.
McDonagh, C. et al. "Optical Chemical Sensors" Chemical Reviews, 2008, 108, pp. 400-422.
Meister, K. et al. "Label-Free Imaging of Metal-Carbonyl Complexes in Live Cells by Raman Microspectroscopy." Angew Chem Int Ed, 2010, 49, pp. 3310-3312.
Miller, E.W. et al. "Boronate-Based Fluorescent Probes for Imaging Cellular Hydrogen. Peroxide." Journal of the American Chemical Society, 2005, 127, pp. 16652-16659.
Motterlini, R. et al. "Therapeutic Applications of Carbon Monoxide-Releasing Molecules." Expert Opinion on Investigational Drugs, 2005, 14, pp. 1305-1318.
Nie, S. et al. "Probing Single Molecules and Single Nanoparticles by Surface-Enhanced Raman Scattering." Science, 1997, 275, pp. 1102-1106.
Niesel, J. et al. "Photoinduced CO Release, Cellular Uptake and Cytotoxicity of a Tris(pyrazolyl)methane (TPM) Manganese Tricarbonyl Complex." Chem Commun (Camb), 2008, pp. 1798-1800.
Njoki, P.N. et al. "Size Correlation of Optical and Spectroscopic Properties for Gold Nanoparticles." Journal of Physical Chemistry C, 2007, 111, pp. 14664-14669.
Oh, W.-K. et al. "Fluorescent Polymer Nanoparticle for Selective Sensing of Intracellular Hydrogen Peroxide." Acs Nano, 2012, vol. 6, No. 10, pp. 8516-8524.
Ott, I. et al. "Modulation of the Biological Properties of Aspirin by Formation of a Bioorganometallic Derivative." Angew Chem Int Ed, 2009, 48, pp. 1160-1163.
Papadopoulou, E. et al. "Label-Free Detection of Single-Base Mismatches in DNA by Surface-Enhanced Raman Spectroscopy." Angewandte Chemie-International Edition, 2011, 50, pp. 9058-9061.
Pfeiffer, H. et al. "Sonogashira and "Click" Reactions for the N-Terminal and Side-Chain Functionalization of Peptides with [Mn(CO)3(tpm)]$^+$-Based CO Releasing Molecules (tpm = tris(pyrazolyl)methane)." Dalton Transactions, 2009, pp. 4292-4298.
Pieczonka, N.P.W. et al. "SERRS for Single-Molecule Detection of Dye-Labeled Phospholipids in Langmuir—Blodgett Monolayers." Langmuir : the ACS Journal of Surfaces and Colloids, 2009, 25, pp. 11261-11264.
Pieczonka, N.P.W. et al. "Single Molecule Analysis by Surfaced-Enhanced Raman Scattering." Chemical Society Reviews, 2008, 37, pp. 946-954.
Piergies, N. et al. "Influence of Substituent Type and Position on the Adsorption Mechanism of Phenylboronic Acids: Infrared, Raman, and Surface-Enhanced Raman Spectroscopy Studies." The Journal of Physical Chemistry A, 2013, pp. 5693-5705.
Policar, C. et al. "Subcellular IR Imaging of a Metal-Carbonyl Moiety Using Photothermally Induced Resonance." Angew Chem. Int Ed, 2011, 50, pp. 860-864.
Poole, L.B. et al. "Discovering Mechanisms of Signaling-mediated Cysteine Oxidation." Current Opinion in Chemical Biology, 2008, 12, pp. 18-24.
Quesada, A.R. et al. "Direct Reaction of $H_2O_2$ with Sulfhydryl Groups in HL-60 Cells: Zinc-Metallothionein and Other Sites." Archives of Biochemistry and Biophysics, 1996, vol. 334, No. 2, Article No. 0452, Oct. 15, pp. 241-250.
Reinemann, D.N. et al. "Vibrational Spectroscopy of N-Methyliminodiacetic Acid (MIDA)-Protected Boronate Ester: Examination of the B—N Dative Bond." The Journal of Physical Chemistry A, 2011, 115, pp. 6426-6431.
Salmain, M. et al. "Use of Fourier Transform Infrared Spectroscopy for the Simultaneous Quantitative Detection of Metal Carbonyl Tracers Suitable for Multilabel Immunoassays." Analytical Biochemistry, 1993, 208, pp. 117-120.
Samanta, A. "Ultrasensitive Near-Infrared Raman Reporters for SERS-Based In Vivo Cancer Detection." Angew Chem Int Ed, 2011, 50, pp. 6089-6092.
Schäferling, M. et al. "Luminescent Probes for Detection and Imaging of Hydrogen Peroxide." Microchimica Acta, 2011, 174, pp. 1-18.
Schlawe, D. et al. "Iron-Containing Nucleoside Analogues with Pronounced Apoptosis-Inducing Activity." Angew Chem Int Ed, 2004, 43, pp. 1731-1734.
Srikun, D. et al. "An ICT-Based Approach to Ratiometric Fluorescence Imaging of Hydrogen Peroxide Produced in Living Cells." Journal of the American Chemical Society, 2008, 130, pp. 4596-4597.
Srikun, D. et al. "Organelle-Targetable Fluorescent Probes for Imaging Hydrogen Peroxide in Living Cells via SNAP-Tag Protein Labelling." Journal of the American Chemical Society, 2010, 132, pp. 4455-4465.
Top, S. et al. "Selective Estrogen-Receptor Modulators (SERMs) in the Cyclopentadienylrhenium Tricarbonyl Series: Synthesis and Biological Behaviour." Chembiochem: a European Journal of Chemical Biology, 2004, 5, pp. 1104-1113.
Uusitalo, L.M. et al. "Recent Advances in Intracellular and In Vivo ROS Sensing: Focus on Nanoparticle and Nanotube Applications." International Journal of Molecular Sciences, 2012, vol. 13, pp. 10660-10679.
Varenne, A. et al. "Quantitative Analysis of Mixtures of Metal-Carbonyl Complexes by Fourier-Transform Infrared Spectroscopy: Application to the Simultaneous Double Immunoassay of Antiepileptic Drugs by the Nonisotopic Carbonyl Metalloimmunoassay Method." Analytical Biochemistry, 1996, 242, pp. 172-179.

(56) References Cited

OTHER PUBLICATIONS

Vessières, A. et al. "Organometallic Estrogens: Synthesis, Interaction with Lamb Uterine Estrogen Receptor, and Detection by Infrared Spectroscopy." Biochemistry, 1988, 27, pp. 6659-6666.
W. E. Smith. "Practical Understanding and Use of Surface Enhanced Raman Scattering/Surface Enhanced Resonance Raman Scattering in Chemical and Biological Analysis." Chemical Society Reviews, 2008, 37, pp. 955-964.
Wolfbeis, O.S. et al. "A Europium-Ion-Based Luminescent Sensing Probe for Hydrogen Peroxide." Angewandte Chemie-International Edition, 2002, 41, pp. 4495-4498.
Yuan, L. et al. "Single Fluorescent Probe Responds to $H_2O_2$, NO, and $H_2O_2$/NO with Three Different Sets of Fluorescence Signals." Journal of the American. Chemical. Society, 2012, 134, pp. 1305-1315.
International Search Report and Written Opinion for International Application No. PCT/SG2014/000437 dated Dec. 8, 2014, 8 pages.

\* cited by examiner

B)

C)

(B)

(C)

(C)

METHOD OF DETECTING HYDROGEN PEROXIDE

CROSS-REFERENCE TO RELATED APPLICATION

This application claims the benefit of priority of Singapore patent application No. 201306961-2 filed on 16 Sep. 2013, the content of which is incorporated herein by reference in its entirety for all purposes.

TECHNICAL FIELD

The invention refers to a method of detecting analytes comprising or consisting of hydrogen peroxide.

BACKGROUND

Surface enhanced Raman spectroscopy (SERS) is an ultra sensitive analytical technique. It is characterized by low background absorption for water, narrow line-widths, and fluorescence quenching, which are important for use as a probe for analysis of biological samples. The Raman signals of probes anchored onto gold or silver nanostructured surfaces may be enhanced by several orders of magnitude (typically $10^6$ to $10^{14}$) because of strong surface plasmon resonance of the nanostructured surface. This signal enhancement has been the basis for chemical sensing applications at lower concentrations but better detection limits, as exemplified in DNA detection, cancer diagnosis, and cellular/intracellular molecules detection.

Over the last few decades, efforts have been made to develop probes for hydrogen ($H_2O_2$) based on chemiluminescence, fluorescence, and electrochemical techniques. However, SERS probes for $H_2O_2$ have not been reported to-date. $H_2O_2$ is a key oxygen metabolite with important physiological and pathological effects in living organisms. In addition to its role as a messenger in cellular signal transduction, an abnormal level of $H_2O_2$ leads to oxidative stress and damage events which are associated with aging, and severe pathologies, such as, cancer, Parkinson's, and Alzheimer's diseases. Furthermore, $H_2O_2$ is also involved in many environmental and industrial food processes.

In view of the above, there remains a need to develop a highly sensitive and selective method for detecting hydrogen peroxide.

SUMMARY

In a first aspect, a method of detecting one or more analytes comprising or consisting of hydrogen peroxide using surface enhanced Raman spectroscopy (SERS) is provided. The method comprises
  a) providing a SERS-active substrate having at least one metal carbonyl cluster compound attached thereon;
  b) contacting one or more analytes with the SERS-active substrate; and
  c) detecting changes in surface enhanced Raman signal from the at least one metal carbonyl cluster compound as an indication of the presence of one or more analytes comprising or consisting of hydrogen peroxide.

BRIEF DESCRIPTION OF THE DRAWINGS

The invention will be better understood with reference to the detailed description when considered in conjunction with the non-limiting examples and the accompanying drawings, in which.

DETAILED DESCRIPTION

Figure 1:
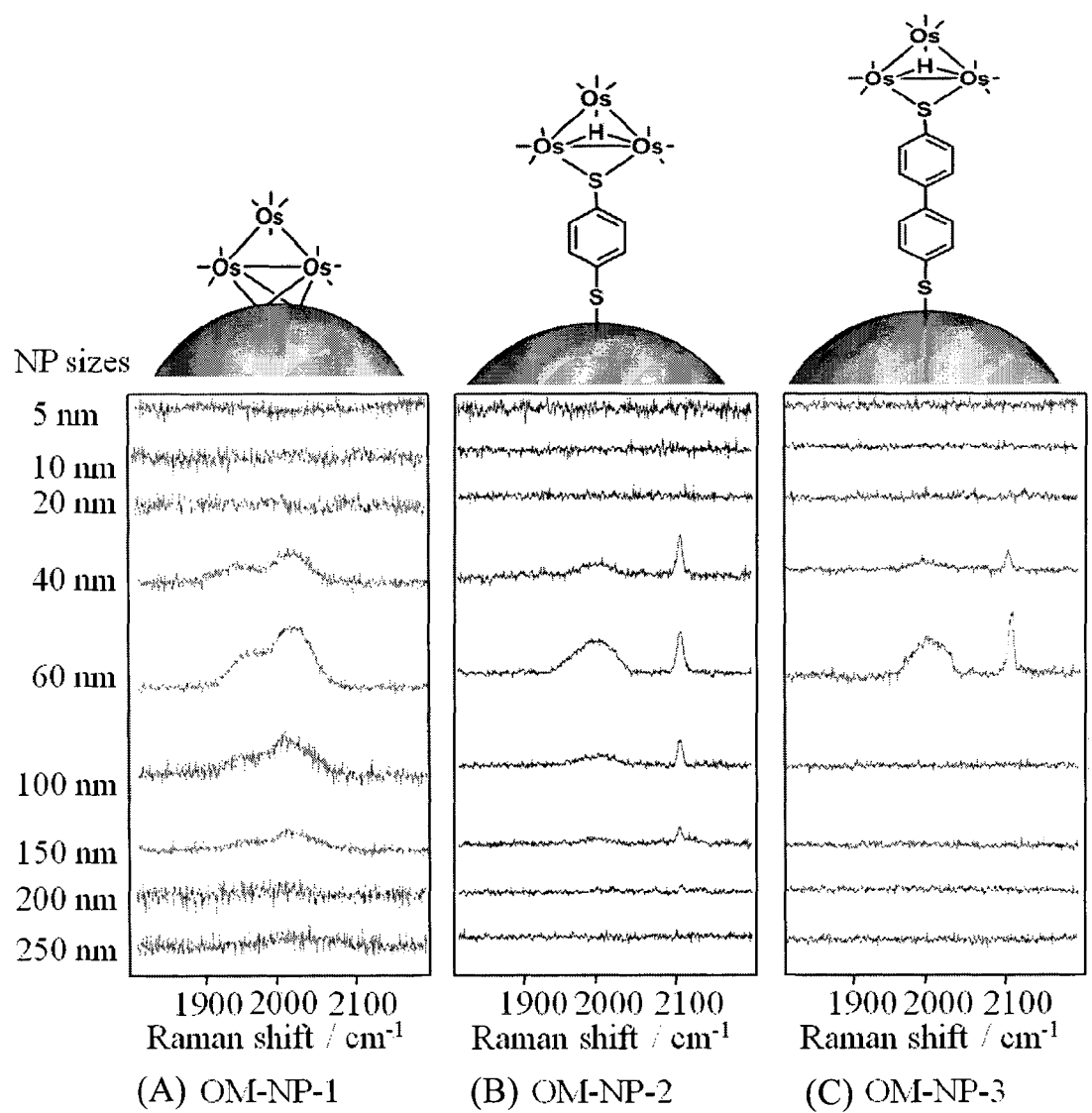
FIG. 1 depicts spectral properties of triosmium carbonyl cluster-nanoparticle (OM-NP) conjugates of (A) $Os_3(CO)_{10}$($\mu$-H)$_2$ (denoted as OM-NP-1); (B) $Os_3(CO)_{10}$($\mu$-H)($\mu$-SC$_6$H$_4$-p-SH) (denoted as OM-NP-2); and (C) $Os_3(CO)_{10}$($\mu$-H)($\mu$-SC$_6$H$_4$—C$_6$H$_4$-p-SH) (denoted as OM-NP-3). SERS spectra of the OM-NP conjugates prepared with different sizes of gold (Au) NPs of 5 nm, 10 nm, 20 nm, 40 nm, 60 nm, 100 nm, 150 nm, 200 nm, and 250 nm in the Raman shift range of 1900 cm$^{-1}$ to 2100 cm$^{-1}$ are shown.

Hydrogen peroxide that is adsorbed on a SERS-active substrate may cause partial electron transfer to take place from the SERS-active substrate to the hydrogen peroxide. As a result, surface potential of the SERS-active substrate may be affected, and a positively charged SERS-active substrate surface may be formed. This may indirectly induce a shift in CO vibrational frequencies of a metal carbonyl cluster compound that is attached to the SERS-active substrate, and/or frequency shift of molecules that are attached on the SERS-active substrate. Using this mechanism, analytes containing hydrogen peroxide may be detected using frequency shift of CO on a SERS-active substrates having at least one metal carbonyl cluster compound attached thereon. Method disclosed herein may also be used for bio-sensing, such as glucose sensing, by detecting hydrogen peroxide that is generated by reacting glucose with an enzyme, glucose oxidase (GOx).

In a first aspect, a method of detecting one or more analytes comprising or consisting of hydrogen peroxide using surface enhanced Raman spectroscopy (SERS) is provided.

The term "detecting" as used herein refers to a method of verifying the presence of a given molecule, and includes in vitro as well as in vivo detection. The detection may also be quantitative, such as correlating the detected signal with amount of analytes present. The method of detecting one or more analytes comprising or consisting of hydrogen peroxide may also be a multiplex method for detecting more than one analyte, such as two or more different analytes. Advantageously, relative sharpness of spectral SERS signal facilitate multiplexing detection since multi-label readouts can be carried out at single excitation wavelength without being limited by spectral overlap.

The method includes providing a SERS-active substrate having at least one metal carbonyl cluster compound attached thereon.

As used herein, the term "metal carbonyl cluster compound" refers to metal cluster compounds comprising carbon monoxide in complex combination with metal atoms, wherein the metal atoms in the metal carbonyl cluster are held together entirely or at least substantially by bonds between metal atoms.

Besides carbonyl ligands, the metal carbonyl compound cluster compound may contain a mix of different ligands. Examples of ligands that may be contained in the metal carbonyl cluster compound include, but are not limited to, aryls such as phenyl, cyclopentadienyl, cyclobutadiene, cyclooctadiene, cyclooctatetraene, phosphate ligands, ethylene, halides such as chloride and iodide, phosphines, phosphites, amines, arsines, stibenes, ethers, sulfides, alkylidenes, nitrites, isonitriles, thiocarbonyls, linear, branched, or cyclic monoalkenes, linear, branched, or cyclic dienes, linear, branched, or cyclic trienes, bicyclic alkenes, bicyclic dienes, bicyclic trienes, tricyclic alkenes, tricyclic dienes, tricyclic trienes, alkynes, and the like.

The ligands of the metal carbonyl compound may be unsubstituted or substituted. As used herein "substituted" refers to a compound or radical substituted with at least one (e.g., 1, 2, 3, 4, 5, 6 or more) substituents independently selected from a halide (e.g., $F^-$, $Cl^-$, $Br^-$, $I^-$), a hydroxyl, an alkoxy, a nitro, a cyano, an amino, an azido, an amidino, a hydrazino, a hydrazono, a carbonyl, a carbamyl, a thiol, a $C_1$ to $C_6$ alkoxycarbonyl, an ester, a carboxyl, or a salt thereof, sulfonic acid or a salt thereof, phosphoric acid or a salt thereof, a $C_1$ to $C_{20}$ alkyl, a $C_2$ to $C_{16}$ alkynyl, a $C_6$ to $C_{20}$ aryl, a $C_7$ to $C_{13}$ arylalkyl, a $C_1$ to $C_4$ oxyalkyl, a $C_1$ to $C_{20}$ heteroalkyl, a $C_3$ to $C_{20}$ heteroaryl (i.e., a group that comprises at least one aromatic ring, wherein at least one ring member is other than carbon), a $C_3$ to $C_{20}$ heteroarylalkyl, a $C_3$ to $C_{20}$ cycloalkyl, a $C_3$ to $C_{15}$ cycloalkenyl, a $C_6$ to $C_{15}$ cycloalkynyl, a $C_5$ to $C_{15}$ heterocycloalkyl, or a combination including at least one of the moieties listed herein, instead of hydrogen, provided that the substituted atom's normal valence is not exceeded.

The carbonyl ligands and/or other ligands such as those mentioned above in the metal carbonyl cluster compound may be bonded to some or all of the metal atoms to form a complex. In some embodiments, a carbonyl ligand is bonded to two metal atoms to form a bridge between the two metal atoms. Other suitable bridging groups may include, for example, phosphine, arsine, and mercapto groups.

Examples of metal carbonyl clusters include, but are not limited to, iron nonacarbonyl ($Fe_2(CO)_9$), cyclopentadienyliron dicarbonyl dimer $[Cp_2Fe(CO)_2]_2$, tetracobalt dodecacarbonyl ($Co_4(CO)_{12}$), ruthenium carbonyl ($Ru_3(CO)_{12}$), hexarhodium hexadecacarbonyl ($Rh_6(CO)_{16}$), osmium carbonyl ($Os_3(CO)_{12}$), iridium carbonyl ($Ir_4(CO)_{12}$), and rhenium carbonyl ($Re_2(CO)_{10}$).

In various embodiments, the at least one metal carbonyl cluster compound has general formula (I)

$$M_3(CO)_xL_{12-x} \quad (I)$$

wherein M at each occurrence denotes a metal selected from Group 6 to Group 11 of the Periodic Table of Elements; x is an integer from 10 to 12; and each L is independently selected from the group consisting of —H and —S—$(C_6H_4)_n$—SH, wherein n is an integer from 1 to 3. CO in formula (I) denotes a carbonyl ligand.

In various embodiments, M is independently selected from the group consisting of chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), and gold (Au). In some embodiments, M is independently selected from the group consisting of Fe, Ru, and Os. In specific embodiments, M is Os.

The metal carbonyl cluster compound may comprise more than one metal. For example, M in the general formula $M_3(CO)_xL_{12-x}$ mentioned above may be represented by $(M_a)_2M_b$, $M_a(M_b)_2$, $(M_b)_2M_c$, $M_b(M_c)_2$, $(M_a)_2M_c$, $M_a(M_c)_2$, or $M_aM_bM_c$, where $M_a$, $M_b$ and $M_c$ denote different metals. In such embodiments, the metal carbonyl compound may have general formula $M_aM_bM_c(CO)_xL_{12-x}$, wherein $M_a$, $M_b$, and $M_c$ denote different metals, and CO, L, and x having the same definitions as that mentioned above.

x is an integer from 10 to 12. For example, x may be 10, 11, or 12. In specific embodiments, x is 10.

L denotes a ligand in the metal carbonyl cluster compound. L at each occurrence may be the same or different. Each L is independently selected from the group consisting of —H and —S—$(C_6H_4)_n$—SH, wherein n is an integer from 1 to 3, such as 1, 2, or 3.

In various embodiments, n is 1 or 2.

In various embodiments, L may be —H, —S—$(C_6H_4)$—SH, or —S—$(C_6H_4)_2$—SH.

In various embodiments, the metal carbonyl cluster compound is selected from the group consisting of $Os_3(CO)_{10}(\mu\text{-H})_2$, $Os_3(CO)_{10}(\mu\text{-H})(\mu\text{-SC}_6H_4\text{-p-SH})$, $Os_3(CO)_{10}(\mu\text{-H})(\mu\text{-SC}_6H_4\text{—C}_6H_4\text{-p-SH})$, and combinations thereof. In the formulas, the symbol "$\mu$" is used to denote a bridging atom. Hence, in the compound $Os_3(CO)_{10}(\mu\text{-H})_2$, H is a bridging atom, while in the compounds $Os_3(CO)_{10}(\mu\text{-H})(\mu\text{-SC}_6H_4\text{-p-SH})$ and $Os_3(CO)_{10}(\mu\text{-H})(\mu\text{-SC}_6H_4\text{—C}_6H_4\text{-p-SH})$, H and S are bridging atoms. In specific embodiments, the metal carbonyl cluster compound is $Os_3(CO)_{10}(\mu\text{-H})_2$.

The at least one metal carbonyl cluster compound is attached to a SERS-active substrate. As used herein, the term "SERS-active substrate" refers to a material which is capable of enhancing Raman scattering.

In various embodiments, the SERS-active substrate comprises one or more metallic nanoparticles. The nanoparticle may assume the form of colloidal metal, hollow or filled nanobars, magnetic, paramagnetic, conductive or insulating nanoparticles, synthetic particles, hydrogel colloids, or bars. In this regard, the metal carbonyl cluster compound functions as a Raman active molecule, while the nanoparticle is Raman enhancing. Further, the nanoparticles may be single nanoparticles or clusters of nanoparticles.

One or a plurality of metallic nanoparticles may be present. The term "plurality" as used herein means more than one, such as at least 2, 20, 50, 100, 1000, 10000, 100000, 1000000, 10000000, or even more.

The metallic nanoparticle may be coated with or consists of a SERS-active material. Examples of a SERS-active material include, but are not limited to, noble metals such as silver, palladium, gold, platinum, iridium, osmium, rhodium, ruthenium; copper, aluminum, or alloys thereof.

For example, the metallic nanoparticle may be formed entirely from a SERS metal, and may for example, consist of a metal selected from the group consisting of a noble metal, copper, aluminum, and alloys thereof. In various embodiments, the metallic nanoparticle is coated with or consists of gold, silver, or alloys thereof. In specific embodiments, the metallic nanoparticle is coated with or consists of gold.

As another example, the metallic nanoparticle may be formed from a non-SERS active material, such as plastic, ceramics, composites, glass or organic polymers, and coated with a SERS metal such as that mentioned above.

In various embodiments, the SERS-active substrate comprises or consists of gold nanoparticles.

Size of the metallic nanoparticle may be characterized by its diameter. The term "diameter" as used herein refers to the maximal length of a straight line segment passing through the center of a figure and terminating at the periphery. In embodiments where a plurality of metallic nanoparticles is present, size of the metallic nanoparticles may be characterized by their mean diameter. The term "mean diameter" refers to an average diameter of the nanoparticles, and may be calculated by dividing sum of the diameter of each nanoparticle by the total number of nanoparticles.

In various embodiments, the metallic nanoparticle or nanoparticles have a diameter or a mean diameter of about 5 nm to about 250 nm. In some embodiments, the metallic nanoparticle or nanoparticles have a diameter or a mean diameter of about 40 nm to about 100 nm, such as about 50 nm to about 100 nm, about 60 nm to about 100 nm, about 40 nm to about 80 nm, about 40 nm to about 70 nm, about 50 nm to about 70 nm, about 40 nm to about 60 nm, or about 60 nm.

In specific embodiments, the SERS active substrate comprises or consists of gold nanoparticles having a mean diameter in the range of about 40 nm to about 100 nm. In specific embodiments, the SERS active substrate comprises or consists of gold nanoparticles having a mean diameter of about 60 nm. Advantageously, it has been found by the inventors that gold nanoparticles with a diameter of 60 nm provide the highest surface enhanced Raman signal intensity as compared to nanoparticles of other diameters.

Where a plurality of metallic nanoparticles is present, the nanoparticles may be monodisperse. The term "monodisperse" refers to nanoparticles having a substantially uniform size and shape. In some embodiments, the standard deviation of diameter distribution of the metallic nanoparticles is equal to or less than 20% of the mean diameter value, such as equal to or less than 15%, 10%, 5% or 3% of the mean diameter value. In some embodiments, the diameter of the metallic nanoparticles is essentially the same.

The metallic nanoparticles may be dispersed in solution or may alternatively be attached on a support. The support that is used to form the SERS-active substrate may generally be formed from any material. Examples of material that may be used to form the support include, but are not limited to, glass, ceramic and organic polymers.

Attachment of the metal carbonyl cluster compound to the SERS-active substrate may be carried out in several ways. For example, the metal carbonyl cluster compound may be attached to surface of a metallic nanoparticle by metal-metal bonding between the metallic nanoparticle and metal atom comprised in the metal carbonyl cluster compound. For such metal-metal bonding, the metallic nanoparticle may serve as a pi ($\pi$) donor by donating a pair of electrons to the d orbital of the metal atom comprised in the metal carbonyl cluster compound, thereby forming metal-metal bond. The mechanism at which the metal atom in the metal carbonyl cluster compound is bonded to the metallic nanoparticle involves covalent bonding. This metal bonding may be strengthened by back donation of electron from the metal carbonyl cluster compound to metallic nanoparticles through antibonding ($\pi^*$) orbital.

$Os_3(CO)_{10}(\mu-H)_2$ is an example of a metal carbonyl compound that is able to be anchored on surface of a metallic nanoparticle by bonding between metal atoms, or termed herein as metal-metal bond. As $Os_3(CO)_{10}(\mu-H)_2$ is electron deficient, and the hydrogen ligands in the compound are highly labile, $Os_3(CO)_{10}(\mu-H)_2$ is very unstable and reactive. The hydrogen ligands are readily displaced by metallic nanoparticles such as gold nanoparticles, and in so doing, osmium atoms are directly bonded via formation of one or more covalent bonds to surface of gold nanoparticles, forming osmium-gold metal-metal bonds.

Additionally or alternatively, the metal carbonyl cluster compound may be attached to the SERS-active substrate by interaction between the SERS-active substrate and ligand comprised in the metal carbonyl cluster compound. For example, the at least one metal carbonyl cluster compound may be stably adsorbed to a surface of the SERS-active substrate by reversible electrostatic interaction, hydrophobic interaction or covalent anchoring. "Electrostatic attraction" relates to attachment via salt bridges, hydrogen bonds and polar interactions, for example, if the surface is charged negative and the compound bears a positive charge, and vice versa. "Hydrophobic interaction" includes the interaction between uncharged and non-polar groups. By attaching the at least one metal carbonyl cluster compound to the SERS-active substrate, Raman signal from the metal carbonyl cluster compound may be enhanced by the SERS-active substrate.

In various embodiments, the at least one metal carbonyl cluster compound is covalently attached to a SERS-active substrate. This may take place by interaction between the SERS-active substrate and ligand comprised in the metal carbonyl cluster compound. To facilitate covalent coupling of the metal carbonyl cluster compound to the surface of the SERS-active substrate, the metal carbonyl cluster compound may include a functional group.

In various embodiments, the metal carbonyl cluster compound comprises a functional group selected from the group consisting of mercapto, carboxy, and amino. For example, the organic ligand comprised in the metal carbonyl cluster compound may comprise a functional group selected from the group consisting of mercapto, carboxy, and amino, for attaching the metal carbonyl cluster compound to the surface of the SERS-active substrate.

A preferred functional group is a mercapto (—SH) group. The terms "thiol group" and "mercapto group" are used interchangeably herein and both relate to the SH group. The mercapto group may facilitate covalent attachment to the metal surface by forming a covalent bond between the sulfur atom and a metal surface atom.

The method of detecting one or more analytes comprising or consisting of hydrogen peroxide includes contacting one or more analytes with the SERS-active substrate. The terms "contacting" or "incubating" as used interchangeably herein refer generally to providing access of one component, reagent, analyte, or sample to another.

Contacting may be carried out by dispensing one or more drops of a sample containing the one or more analytes to the SERS-active substrate. The solution comprising the analyte or sample may also comprise another component or reagent, such as dimethyl sulfoxide (DMSO) or a detergent, which facilitates mixing, interaction, uptake, or other physical or chemical phenomenon advantageous to the contact between the analytes and/or samples.

In various embodiments, contacting one or more analytes with the SERS-active substrate include incubating the one or more analytes with the SERS-active substrate. The one or more analytes and the at least one metal carbonyl cluster compound may be incubated for a suitable time period that allows interaction between the analyte and the SERS-active substrate, which may be in the order of minutes. In specific embodiments, incubating the one or more analytes with the at least one metal carbonyl cluster compound is carried out for about 5 minutes at ambient temperature, which generally refers to a temperature of between about 20° C. to about 40° C.

In various embodiments, contacting the one or more analytes with the SERS-active substrate is carried out without any chemical reaction taking place between the SERS-active substrate and/or the metal carbonyl cluster compound. After contacting the one or more analytes with the SERS-active substrate, changes in surface enhanced Raman signal from the at least one metal carbonyl cluster compound are detected as an indication of the presence of the one or more analytes comprising or consisting of hydrogen peroxide.

In various embodiments, detecting changes in surface enhanced Raman signal from the at least one metal carbonyl cluster compound comprises at least one of (i) detecting changes in pattern and/or intensity of SERS signal in the region of 1800 cm$^{-1}$ to 2200 cm$^{-1}$; and (ii) detecting peak shifts in surface enhanced Raman spectrum from the at least one metal carbonyl cluster compound as an indication of the presence of the one or more analytes.

Advantageously, the at least one metal carbonyl cluster compound is able to provide a unique SERS signal at a region of 1800 cm$^{-1}$ to 2200 cm$^{-1}$, thereby avoiding interference with signals emitted by biomolecules which are in the 800 cm$^{-1}$ to 1800 cm$^{-1}$ region. This allows identification of biomolecules without the need to decouple signals emitted from the metal carbonyl cluster compound. This attribute may be used to provide a more complex spectrum for multiplex detection.

Use of metal carbonyl cluster compounds also addresses challenges posed by use of fluorescent probes containing functional groups, such as boronate (1370 cm$^{-1}$) and aromatic (1580 cm$^{-1}$) groups, which are used to react with $H_2O_2$, as such probes are encumbered by interference signals from biomolecules which tend to be in the 400 cm$^{-1}$ to 1800 cm$^{-1}$ region.

In various embodiments, detecting changes in surface enhanced Raman signal from the at least one metal carbonyl cluster compound includes detecting peak shifts in surface enhanced Raman spectrum from the at least one metal carbonyl cluster compound as an indication of the presence of the one or more analytes.

As mentioned above, hydrogen peroxide that is adsorbed on a SERS-active substrate may cause partial electron transfer to take place from the SERS-active substrate to the hydrogen peroxide. The analytes comprising or consisting of hydrogen peroxide do not react directly with the metal carbonyl cluster compounds. Instead, they exert a positive potential on the SERS-active substrate, and in so doing, induce a positive charge on the metal atoms comprised in the metal carbonyl cluster compounds. As a result, surface potential of the SERS-active substrate may be affected, and a positively charged SERS-active substrate surface may be formed. The change in surface potential results in vibrational frequency shifts of CO in metal carbonyl cluster compounds that are attached onto the SERS-active substrate. An increase in CO bond order and a blue-shift in the CO vibrations may result.

Without wishing to be bound by theory, the vibrational frequency shifts of CO may be explained by nature of the metal-CO bonds present in metal carbonyl cluster compounds. Metal-CO bonding comprises a metal-to-CO σ donation and a CO-to-metal π back-donation. The former interaction involves electron-donation into a slightly antibonding σ* orbital of CO, and the latter involves electron-donation out of a pair of bonding π orbitals of CO. A positive potential on the SERS-active substrate surface, for example, may induce a positive charge on metal atom of the metal carbonyl cluster compound, which may in turn lead to a decrease in σ donation and increase in π back-donation. Both changes may result in an increase in the CO bond order, and hence vibrational frequency of CO.

Further, as mentioned above, method disclosed herein may also be used for bio-sensing. By detecting hydrogen peroxide that is generated from reacting compounds which generate hydrogen peroxide upon reaction with a suitable enzyme, with an enzyme, the compounds may be detected and/or identified.

In various embodiments, contacting one or more analytes with the SERS-active substrate is carried out in the presence of a suitable enzyme. An enzyme may be used when the one or more analytes comprising or consisting of hydrogen peroxide comprises or consists of a compound which generates hydrogen peroxide upon reaction with the enzyme. Advantageously, this expands the number or scope of analytes that may be detected using the method disclosed herein.

For example, the compound which generates hydrogen peroxide upon reaction with the enzyme may be selected from the group consisting of glucose, uric acid, lactate, glutamate, and cholesterol. Depending on the compound used, different enzymes may be suitable. For example, urate oxidase may be used for uric acid; lactate oxidase for lactate, L-glutamate oxidase for glutamate, and cholesterol oxidase for cholesterol. In various embodiments, the compound which generates hydrogen peroxide upon reaction with the enzyme comprises or consists of glucose. Accordingly, the enzyme which may be used to react with glucose may be glucose oxidase.

As previously mentioned, detecting changes in surface enhanced Raman signal from the at least one metal carbonyl cluster compound may include detecting changes in pattern and/or intensity of SERS signal in the region of 1800 cm$^{-1}$ to 2200 cm$^{-1}$ as an indication of the presence of the one or more analytes. This may be used to detect analytes having a thiol group, which may be carried out in addition to or apart from detecting analytes containing hydrogen peroxide.

In various embodiments, the method of detection disclosed herein is also used to detect one or more analytes comprising a thiol group. The method may further comprise providing at least one unbound metal carbonyl cluster compound and allowing the one or more analytes to react with the at least one unbound metal carbonyl cluster compound prior to providing a SERS-active substrate having at least one metal carbonyl cluster compound attached thereon.

Metal carbonyl cluster compounds, such as OM-NP-1 disclosed in the examples, may exhibit high reactivity towards thiols, and form thiolated-bridged clusters. Formation of such thiolated-bridged clusters may result in changes in spectra for CO stretching vibrations, characterized by a very intense peak at about 2111 cm$^{-1}$. By detecting frequency shifts of the characteristic peak upon reaction of the metal carbonyl cluster compounds with thiols, the method disclosed herein may form the basis of a detection system for biologically important thiols. Advantageously, this allows dual detection of analytes containing a thiol group as well as analytes containing hydrogen peroxide to be carried out.

As mentioned above, hydrogen peroxide is a key oxygen metabolite with important physiological and pathological effects in living organisms. In addition to its role as a messenger in cellular signal transduction, an abnormal level of $H_2O_2$ leads to oxidative stress and damage events which are associated with aging, and severe pathologies, such as, cancer, Parkinson's, and Alzheimer's diseases. The method of detection disclosed herein may be used to detect hydrogen peroxide within cells, whereby the hydrogen peroxide may be provided in one or more living cells.

In various embodiments, the one or more analytes comprising or consisting of hydrogen peroxide is contained in a sample and the detection is in vitro.

The term "sample", as used herein, refers to an aliquot of material, frequently biological matrices, an aqueous solution or an aqueous suspension derived from biological material.

Samples to be assayed for the presence of an analyte include, for example, cells, tissues, homogenates, lysates, extracts, and purified or partially purified proteins and other biological molecules and mixtures thereof.

Non-limiting examples of samples include human and animal body fluids such as whole blood, serum, plasma, cerebrospinal fluid, sputum, bronchial washing, bronchial aspirates, urine, semen, lymph fluids and various external secretions of the respiratory, intestinal and genitourinary tracts, tears, saliva, milk, white blood cells, myelomas and the like; biological fluids such as cell culture supernatants; tissue specimens which may or may not be fixed; and cell specimens which may or may not be fixed. The samples used may vary based on the assay format and the nature of the tissues, cells, extracts or other materials, especially biological materials, to be assayed. Methods for preparing protein extracts from cells or samples are well known in the art and can be readily adapted in order to obtain a sample that may be used in the method disclosed herein.

The one or more analytes comprising or consisting of hydrogen peroxide may be detected in a body fluid comprising the analyte. In specific embodiments, the body fluid is selected from the group consisting of plasma, serum, blood, lymph, liquor and urine. Detection in a body fluid may also be in vivo, i.e. without first collecting a sample.

The method disclosed herein may be used, for example, in cancer assay such as ovarian cancer test through the $H_2O_2$ production of haptaglobin (biomarker).

Apart from the above, the method disclosed herein may also be used in detection of $H_2O_2$ in environmental and industrial food processes.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

As used herein, the term "and/or" includes any and all combinations of one or more of the associated listed items. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

A novel label-free detection system based on OM-NP constructs was used for the direct measurement of $H_2O_2$. It has been demonstrated herein that the vibration frequency of CO on OM-NP is sensitive to $H_2O_2$ based on changes of surface potential of OM-NP constructs by $H_2O_2$. This property has been applied further to biosensing such as enzymatic glucose sensing for the detection of spiked glucose concentration in clinical urine sample. It has been demonstrated herein that OM-NP constructs is a promising tool for clinical diagnosis of $H_2O_2$ and glucose. This sensing strategy could be potentially applied to other metal carbonyl compounds and to determine many other analytes, such as uric acid, lactate, glutamate, and cholesterol, when performed in conjunction with suitable enzymes.

Together with hollow core photonic crystal fiber (HC-PCF) for SERS detection, this constitutes an ultra-low-volume (about 50 nL) and highly sensitive detection method for $H_2O_2$ in cells, and for enzymatic glucose detection. The known chemistry of the precursor compound used in the synthesis of the OM-NP conjugate also allowed for the development of a novel protocol for the simultaneous SERS detection of $H_2O_2$ and thiol biomolecules.

Example 1: General Procedure

All manipulations for chemical synthesis were carried out using standard Schlenk techniques under an argon or nitrogen atmosphere as will be known to a person skilled in the art.

The triosmium carbonyl cluster 1, $Os_3(CO)_{10}(\mu-H)_2$, was prepared according to the following. Briefly, $Os_3(CO)_{12}$ in dichloromethane was reacted with trimethylamine oxide in methyl alcohol in the presence of a little methyl cyanide at room temperature to yield almost quantitatively the methyl cyanide complex [OS$_3$(CO)$_{11}$(NCMe)]. Reaction of [OS$_3$(CO)$_{11}$(NCMe)] with H$_2$ gave Os$_3$(CO)$_{10}$(μ-H)$_2$. Os$_3$(CO)$_{12}$ was purchased from Oxkem; all other chemicals were purchased from other commercial sources and used as supplied.

UV-vis spectra were recorded using a Beckman Coulter DU 730 spectrometer. Infrared spectra were recorded on a Bruker Alpha FT-IR spectrometer. Solution spectra were recorded in DCM solution, in a solution IR cell with NaCl windows and a path length of 0.1 mm, at a resolution of 2 cm$^{-1}$. HRMS were recorded in ESI mode on a Waters UPLC-Q-Tof MS mass spectrometer.

The spectral measurements were carried out using a Renishaw InVia Raman (UK) microscope with a Peltier cooled CCD detector and an excitation wavelength at 633 nm, where the laser beam is directed to the sample through a 50× objective lens, which was used to excite the sample and also to collect the return Raman signal. The maximum laser power at the sample was measured to be 6.2 mW and the exposure time was set at 10s throughout the measurements. Prior to each measurement, the instrument was calibrated with a silicon standard whose Raman peak is centered at 520 cm$^{-1}$. All Raman spectra were processed with the WiRE3.0 software, with curve fitting at a spectral resolution of 0.6 cm$^{-1}$.

TEM images were recorded on a JEOL JEM-1010 transmission electron microscope at an accelerating voltage of 300 kV; the samples were prepared by placing a drop (2.5 μl) of the nanoparticles onto a 200-mesh nickel-coated grid, and the grid containing the nanoparticles was dried prior to use. Mean particle sizes were obtained by measuring the sizes of the nanoparticles in a few randomly chosen areas of the digitized image, each containing approximately 100 to 200 nanoparticles.

Dark field images were taken with an enhanced dark-field illumination system (CytoViva, Auburn, Ala.) attached to a Nikon LV100 microscope. The system comprised a dark-field condenser (CytoViva) attached via a fiber optic light guide to a 24 W metal halide light source (Solarc Lighting Technology). Images were acquired at 300 ms exposure time using a Nikon objective lens (100×, NA 1.25 and WD 0.23, oil lens) and a Nikon DS-Fi1 camera with the associated software (NIS-ElementsD).

Example 2: Syntheses of Os$_3$(CO)$_{10}$(μ-H)(μ-SC$_6$H$_4$-p-SH) (2) and Os$_3$(CO)$_{10}$(μ-H)(μ-SC$_6$H$_4$—C$_6$H$_4$-p-SH) (3)

A sample of Os$_3$(CO)$_{10}$(NCCH$_3$)$_2$ (45 mg, 0.048 mmol) and 1,4-benzenedithiol (27 mg, 0.19 mmol) were dissolved in DCM (6 mL) and left to stir at room temperature overnight. Solvent was removed in vacuo and the yellow residue was purified by TLC on silica using hexane:DCM (1:1, v/v) as eluent to yield cluster 2 as the major yellow band (R$_f$=0.52).

Yield: 30 mg (63%)
IR (DCM, cm$^{-1}$): 2109w, 2068s, 2059m, 2023s, 2000m, 1985w.
$^1$H NMR (400 MHz, CDCl$_3$): δ 7.20-7.13 (m, 4H, Ar), 3.49 (s, 1H, SH), −17.04 (s, 1H, OsHOs).
$^{13}$C{$^1$H} NMR (100 MHz, CDCl$_3$): δ 180.70, 180.19, 176.10, 173.99, 172.17, 169.34, 169.25, 142.54, 132.96, 132.21, 129.03.

A similar reaction between Os$_3$(CO)$_{10}$(NCCH$_3$)$_2$ (39 mg, 0.042 mmol) and biphentl-4,4'-dithiol (37 mg, 0.17 mmol) gave, after TLC separation using hexane:DCM (3:1, v/v) as eluent, cluster 3 as the major yellow band (R$_f$=0.38).

Yield: 25 mg (56%)
IR (DCM, cm$^{-1}$): 2109w, 2068s, 2059m, 2023s, 2001m, 1984w.
$^1$H NMR (400 MHz, CDCl$_3$): δ 7.48-7.32 (m, 8H, Ar), 3.50 (s, 1H, SH), −17.00 (s, 1H, OsHOs).
$^{13}$C{$^1$H} NMR (100 MHz, CDCl$_3$): δ 180.74, 180.26, 176.16, 174.05, 172.20, 169.34, 144.34, 141.19, 137.20, 132.12, 131.12, 129.93, 127.84, 126.86.

Example 3: Preparation of OM-NP Conjugates

Freshly prepared solutions of clusters in ethanol (10 μL, 100 μM) were mixed with different sizes of gold NPs (1 mL, 2.6×10$^{10}$ particles/mL, BBInternational UK) in ethanol. After incubating for 60 min, they were pelleted by centrifuge and re-suspended in DI water (100 μL). Excess of ethanol was removed by argon flow. The pelleting and re-suspension was repeated, to remove unbound clusters and finally re-suspended in DI water (100 μL) for the SERS measurements.

Three different OM-NP conjugates, labeled OM-NP-1, OM-NP-2 and OM-NP-3, were prepared from three different triosmium carbonyl clusters, Os$_3$(CO)$_{10}$(μ-H)$_2$ (1), Os$_3$(CO)$_{10}$(μ-H)(μ-SC$_6$H$_4$-p-SH) (2), and Os$_3$(CO)$_{10}$(μ-H)(μ-SC$_6$H$_4$—C$_6$H$_4$-p-SH) (3), respectively, and gold nanoparticles with diameters ranging from 5 nm to 250 nm.

Figure 2:
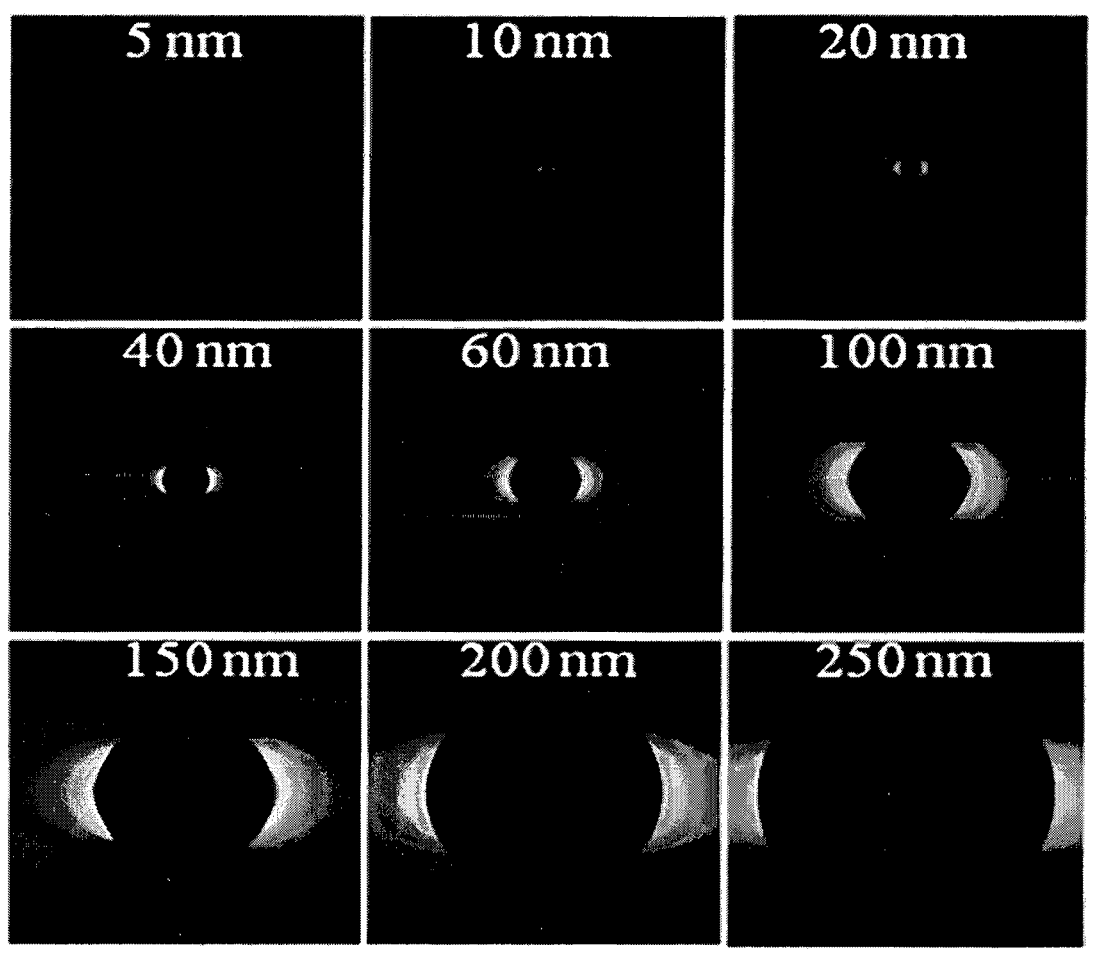
FIG. 2 depicts finite elements method (FEM) modeling of electromagnetic field intensity around gold nanoparticles (NPs) of different sizes of 5 nm, 10 nm, 20 nm, 40 nm, 60 nm, 100 nm, 150 nm, 200 nm, and 250 nm (strong field corresponds to large enhancements of SERS signals).

In these OM-NP conjugates, the linker groups present in 1 to 3 determined the distance of the cluster core from the gold NP surface. The CO stretching vibrations of these conjugates in their SERS spectra revealed that optimal signal intensity enhancement was obtained with 60 nm NPs; signals were observable with NPs of size from about 40 nm onwards, but the intensity for sizes greater than 100 nm was weak (FIG. 1). This is similar to the reported optimal size range of gold NPs for SERS enhancement, and is also supported by results from a simulation of the electric field which were carried out (FIG. 2).

Among the three conjugates, the OM-NP-1 conjugate with the 60 nm NPs gave the highest intensity, demonstrating that the peak intensity decreased with increasing distance of the cluster from the surface, showing that the enhancement factor decays rapidly with increasing distance between the tag and the nanoparticle surface. All subsequent experiments were thus carried out with 60 nm NPs.

Figure 3:
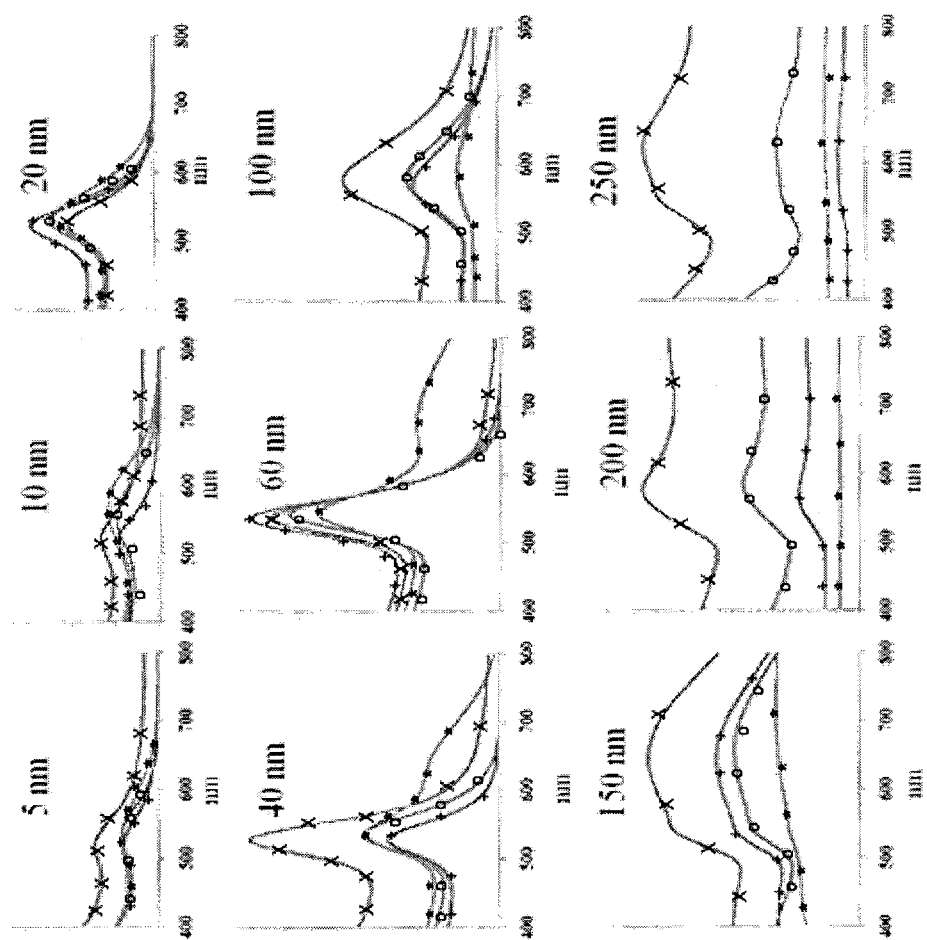
FIG. 3 depicts UV-vis spectra of different sizes of gold NPs and OM-NP conjugates of 5 nm, 10 nm, 20 nm, 40 nm, 60 nm, 100 nm, 150 nm, 200 nm, and 250 nm. X-axis denotes wavelength in nm in the range of 400 nm to 800 nm. Legend of the curves in the graphs: gold NP, OM-NP-1, OM-NP-2 and OM-NP-3.
Figure 4:
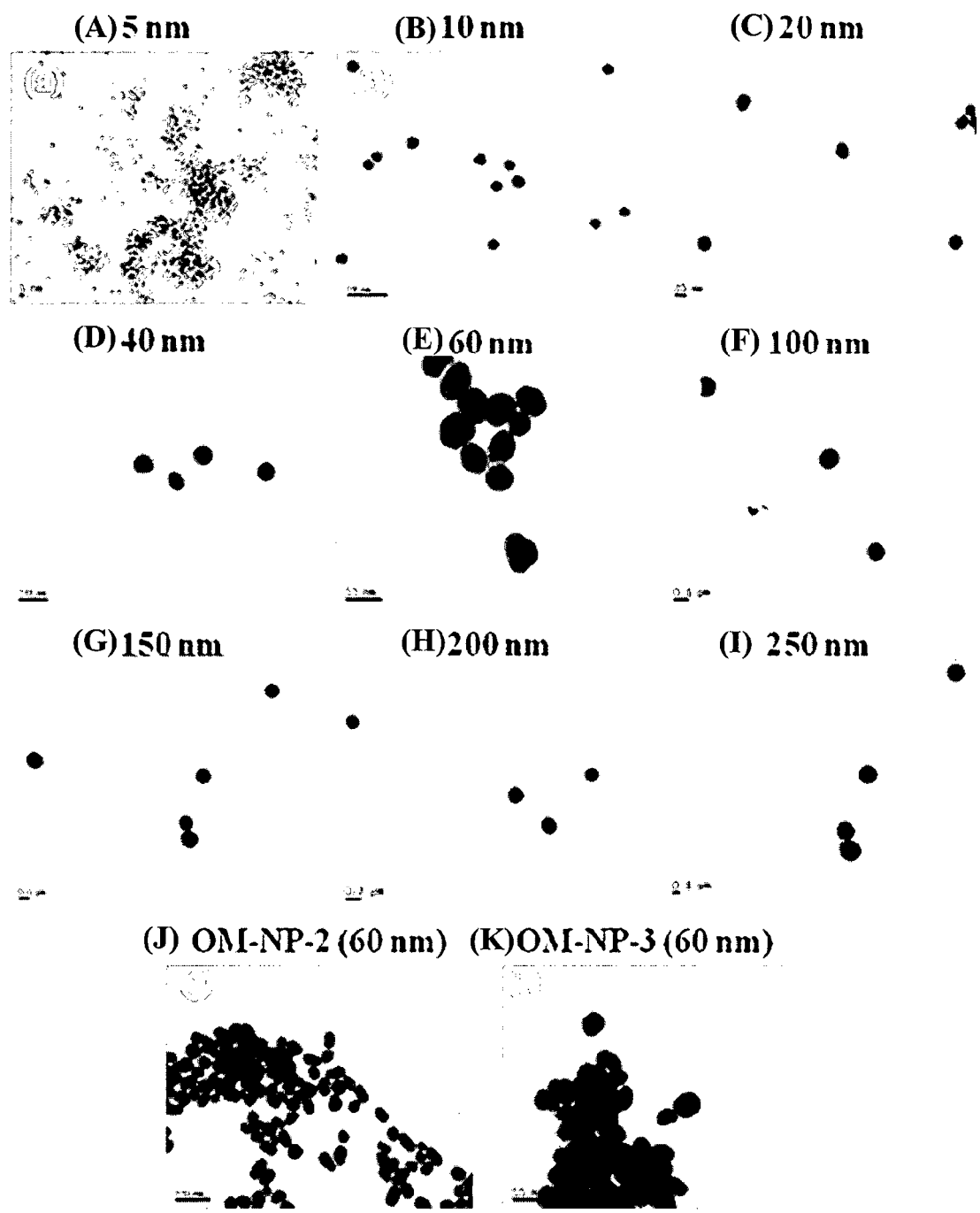
FIG. 4 shows transmission electron microscopy (TEM) images of different size of OM-NP-1 for (A) 5 nm, (B) 10 nm, (C) 20 nm, (D) 40 nm, (E) 60 nm, (F) 100 nm, (G) 150 nm, (H) 200 nm, (I) 250 nm; (J) aggregation of OM-NP-2 at 60 nm NPs size, and (K) aggregation of OM-NP-3 at 60 nm NPs size. Scale bar in the figures denote: (A) 5 nm, (B) 50 nm, (C) 20 nm, (D) 100 nm, (E) 50 nm, (F) 0.1 µm, (G) 0.1 µm, (F) 0.2 µm, (I) 0.1 µm, (J) 100 nm and (K) 50 nm.

The SERS spectrum of OM-NP-1 also showed the smallest change in intensity with a change in size of the gold NPs, compared to OM-NP-2 and OM-NP-3. This was corroborated by their UV-vis spectra, which showed a similar trend (FIG. 3), and may be attributed to aggregation of the gold NPs. Indeed, the TEM images (FIG. 4) showed that while OM-NP-1 displayed spherical or faceted but monodispersed particles, aggregation was obvious with OM-NP-2 and OM-NP-3.

Example 4: Electric Field Simulation for Gold Nanoparticles

A Lenovo desktop, Intel® Core™$_2$ Quad CPU Q9650 running at 3.00 GHz with 8 GB RAM, was used to perform high-mesh-density simulations. The operating platform is 64-bit Windows 7 Professional. For simulation of the plasmonic properties of the gold nanoparticles, an RF extended module under COMSOL Multiphysics 3.5a version, was used. The desired particle size and 3D shape were drawn under Draw Mode using the Cartesian coordinate system.

Boundary conditions and perfectly matched layer (PML) were also defined in the draw mode. Simulation duration for a single nanoparticle took about 4 h.

Example 5: Studies on OM-NP Conjugates with $H_2O_2$ and pH

SERS spectrum of OM-NP constructs with $H_2O_2$ and varied pH solution was subsequently measured. A sample of the freshly prepared 60 nm OM-NP conjugates (20 µL) was incubated (5 min) with different concentrations of $H_2O_2$ or pH solution (10 µL) for 10 min. SERS signal of the OM-NP constructs was then obtained upon excitation with a 785 nm laser (300 mW power). The SERS signal of the OM-NP constructs was measured.

UV irradiation was carried out using an Ultra-Violet Products Pen-Ray® mercury lamp, with power consumption at 5.5 W and principal output wavelength at 254 nm. The OM-NP conjugate was placed in a photochemical reaction flask with an immersion well for the UV lamp.

Example 6: SERS Spectrum Study on $Os_3(CO)_{12}$ Treated with $H_2O_2$

A solution of $Os_3(CO)_{12}$ in ethanol (200 µL) was incubated (5 min) with $H_2O_2$ (100 µL, 20 µM). The gold NP solution (100 µL) was added after the incubation and the SERS spectrum measured.

Figure 5:
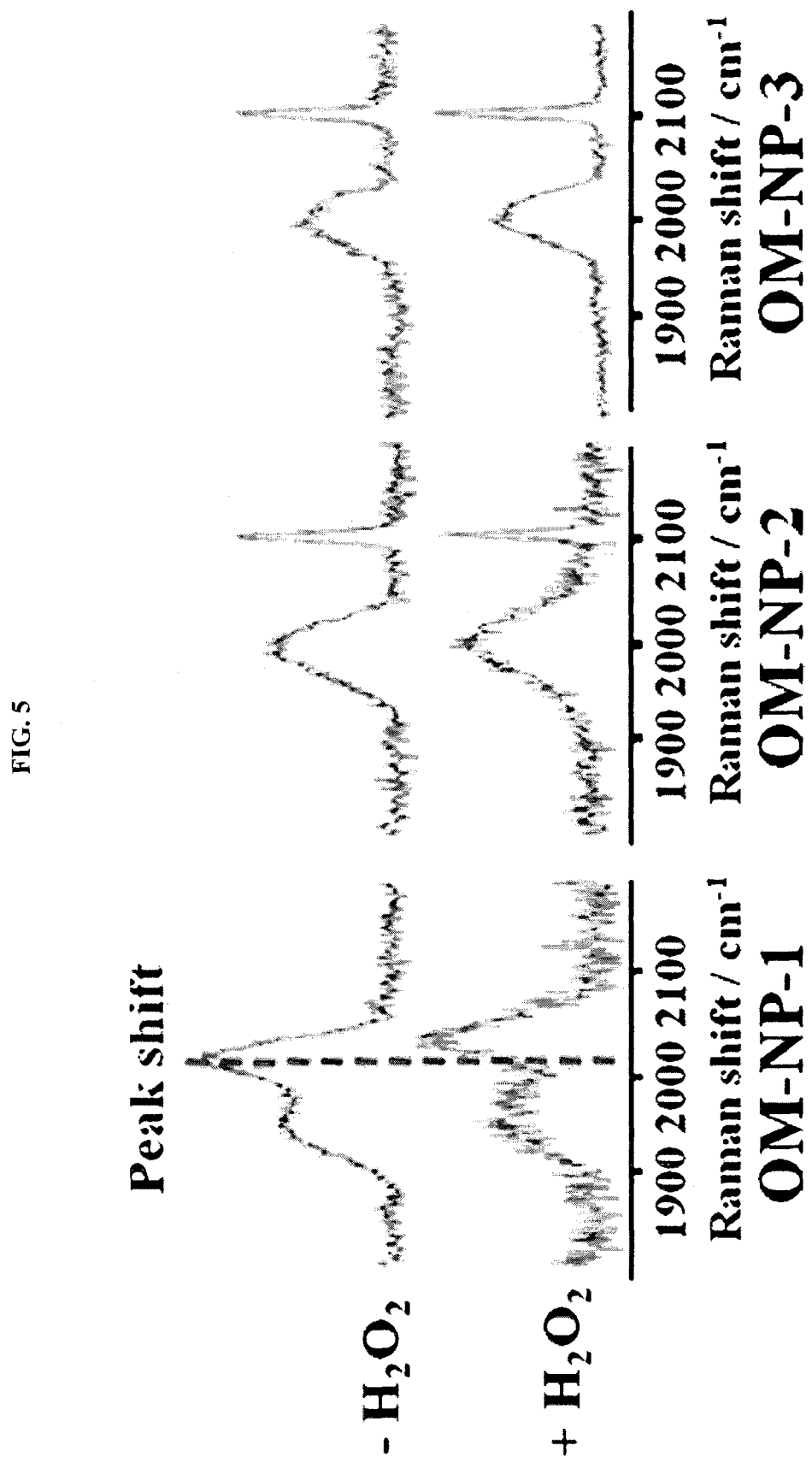
FIG. 5 shows SERS spectra of OM-NP conjugates of OM-NP-1, OM-NP-2 and OM-NP-3 with (+$H_2O_2$) and without (−$H_2O_2$) addition of $H_2O_2$ in the Raman shift range of 1900 cm$^{-1}$ to 2100 cm$^{-1}$. As shown in the figure, there is a shift in peak for OM-NP-1 when $H_2O_2$ was added.
Figure 6:
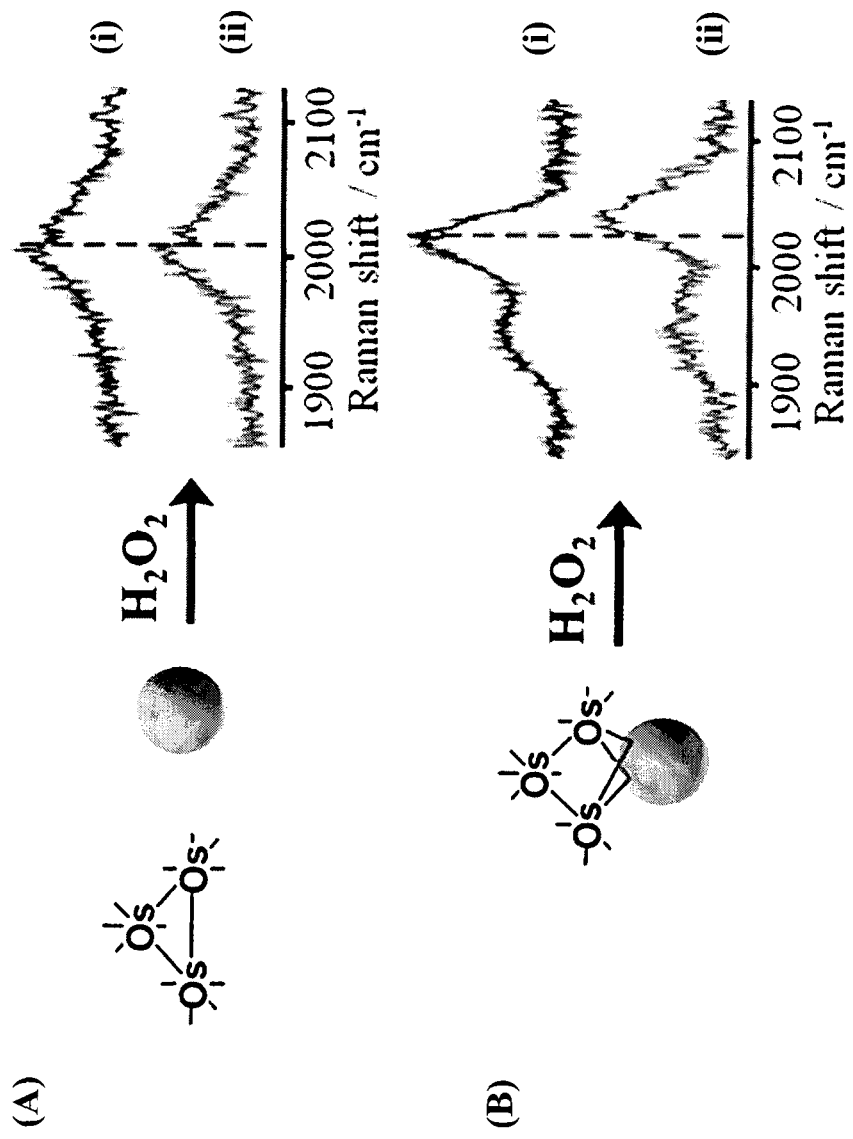
FIG. 6 shows SERS spectra of (A) $Os_3(CO)_{12}$ with Au NP, and (B) OM-NP-1, for (i) without, and (ii) with $H_2O_2$ in the range of 1900 cm$^{-1}$ to 2100 cm$^{-1}$. As shown in the figure, there is a shift in peak for OM-NP-1 when $H_2O_2$ was added, where such a shift is not present in (A) where $Os_3(CO)_{12}$ is not conjugated to Au NP.

Addition of $H_2O_2$ (20 µM) to OM-NP-1 resulted in an instantaneous blue shift of the CO peak, but with OM-NP-2 and OM-NP-3, no significant change was observed (FIG. 5), indicating that the OM-NP-1 conjugates were most suitable for $H_2O_2$ sensing. The SERS spectrum of $Os_3(CO)_{12}$ treated with hydrogen peroxide showed no difference from that without (FIG. 6), confirming that $H_2O_2$ did not react directly with the triosmium cluster, in accord with the known reactivity of these clusters.

Figure 7:
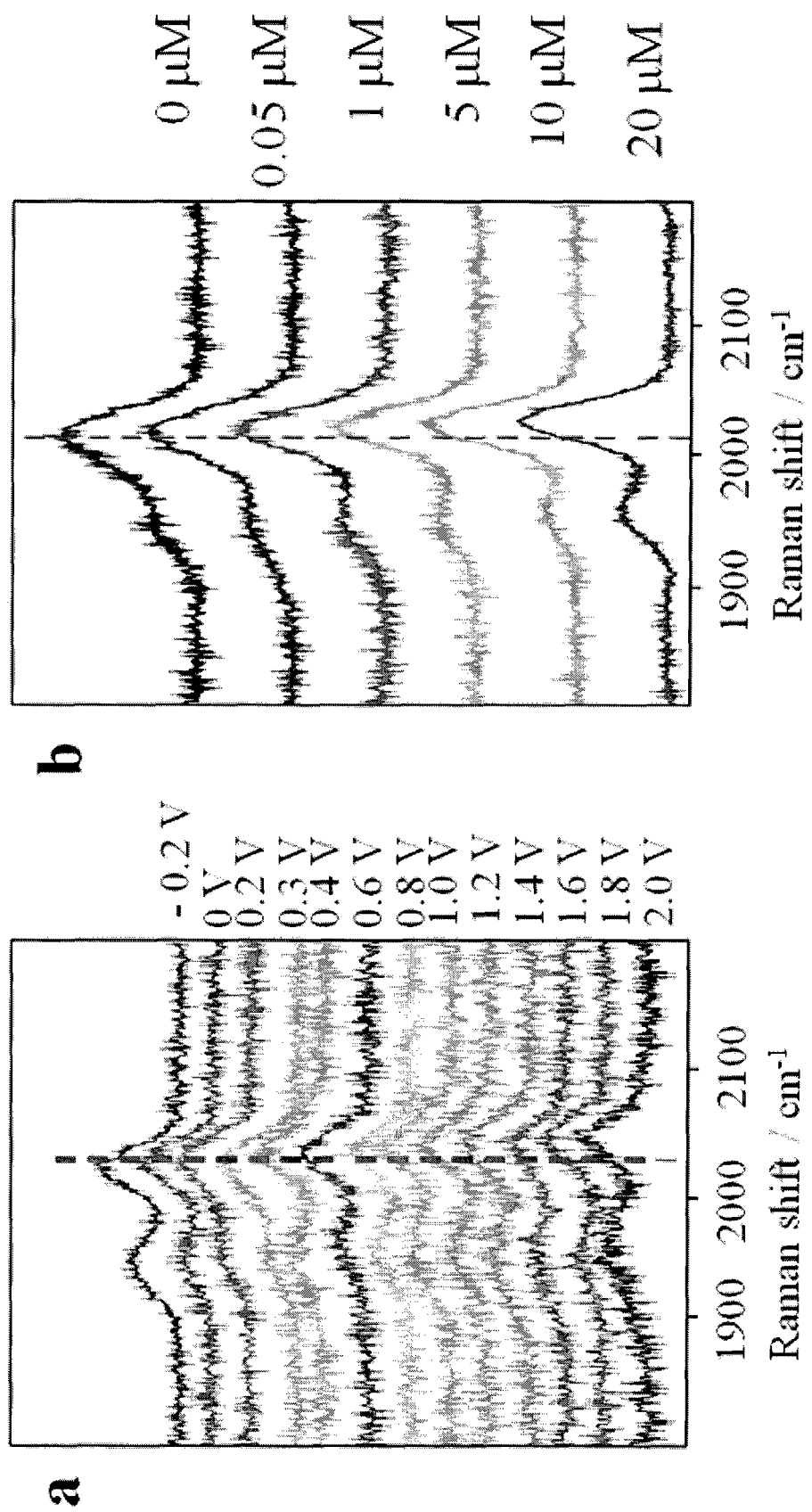
FIG. 7 depicts spectral properties of OM-NP-1, where (A) shows potential-dependent SERS spectra of OM-NP-1 immobilized on gold film electrode for −0.2 V, 0 V, 0.2 V, 0.3 V, 0.4 V, 0.6 V, 0.8 V, 1.0 V, 1.2 V, 1.4 V, 1.6 V, 1.8 V, and 2.0 V in the Raman shift range of 1900 cm$^{-1}$ to 2100 cm$^{-1}$; and (B) shows SERS responses of OM-NP-1 to $H_2O_2$ of different concentrations of 0 µM, 0.05 µM, 1 µM, 5 µM, 10 µM, and 20 µM in the Raman shift range of 1900 cm$^{-1}$ to 2100 cm$^{-1}$.
Figure 8:
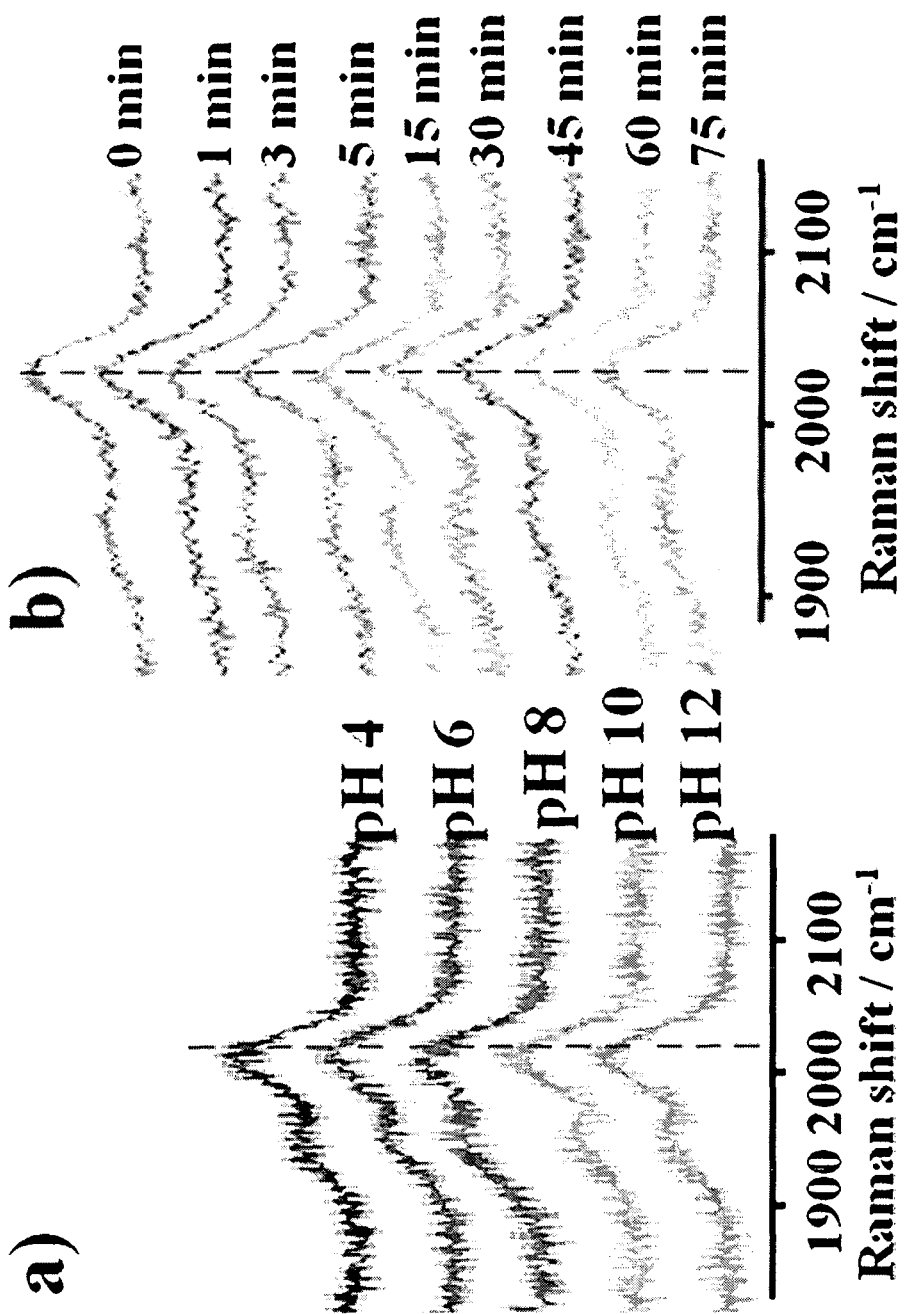
FIG. 8 shows SERS response of OM-NP-1 to (A) different pH of 4, 6, 8, 10, and 12 in the Raman shift range of 1900 cm$^{-1}$ to 2100 cm$^{-1}$, and (B) different lengths of UV irradiation of 0 min, 1 min, 3 min, 5 min, 15 min, 30 min, 45 min, 60 min, and 75 min in the Raman shift range of 1900 cm$^{-1}$ to 2100 cm$^{-1}$.
Figure 9:
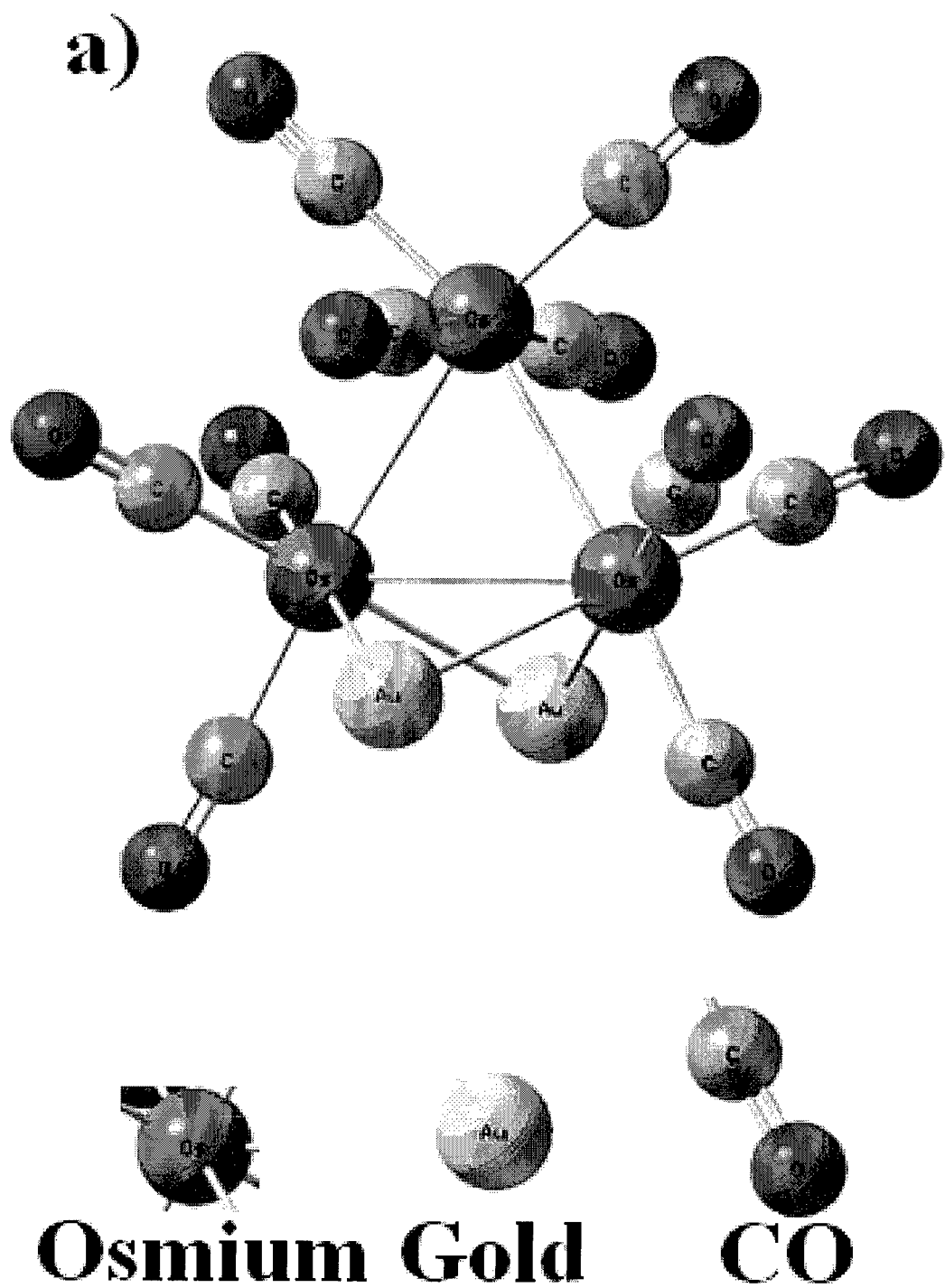
FIG. 9 shows (A) molecular structure of the $Os_3(CO)_{10}$($\mu$-Au)$_2$ model used in the computational study, and calculated Raman spectra ($v_{CO}$) for (B) neutral $Os_3(CO)_{10}$($\mu$-Au)$_2$, and (C) [$Os_3(CO)_{10}$($\mu$-Au)$_2$]$^+$. X-axis for (B) and (C) denote frequency (cm') in the range of 1800 cm$^{-1}$ to 2150 cm$^{-1}$.
Figure 9:
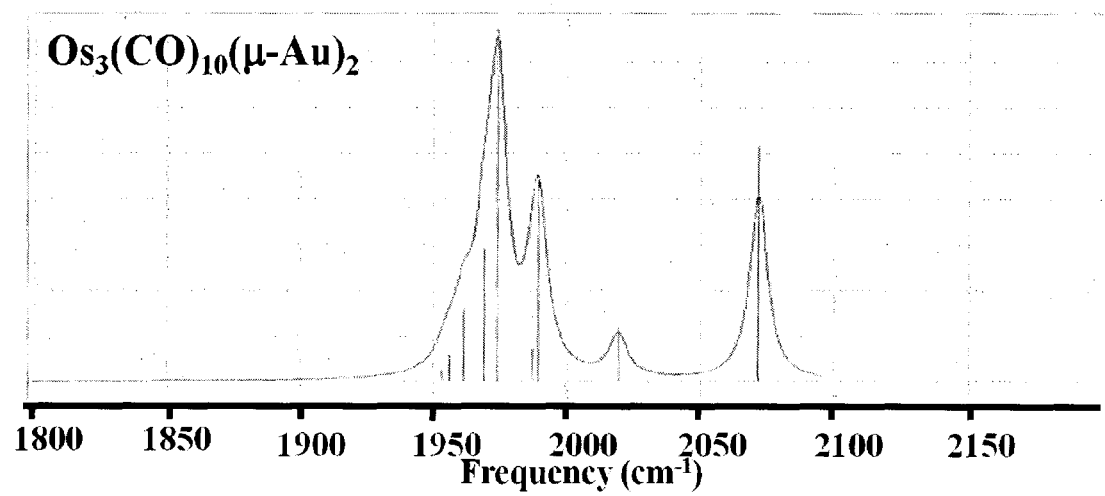
Figure 9:
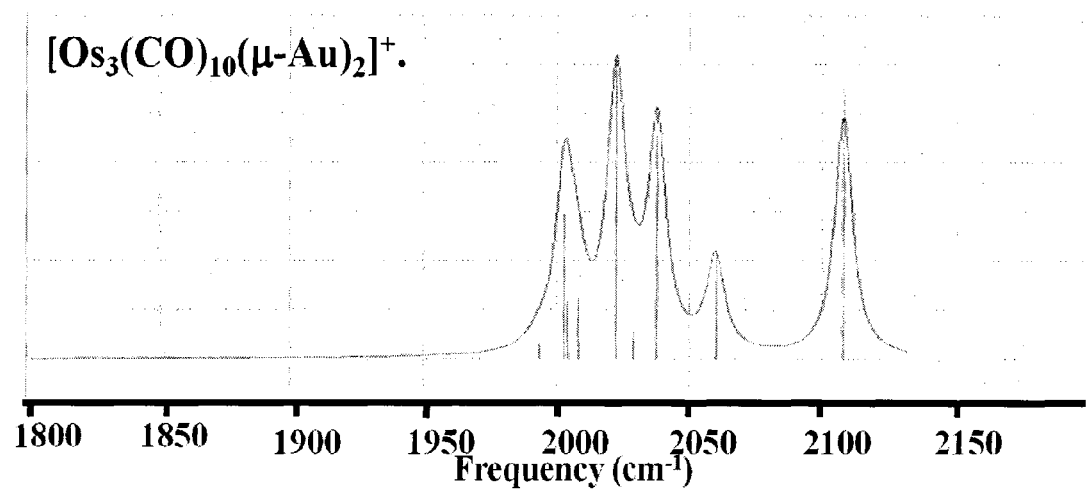

A sample of the OM-NP-1 conjugates immobilized onto a gold film electrode showed that while the peak pattern remained, there was a noticeable peak shift (from 2016 $cm^{-1}$ to 2046 $cm^{-1}$) when the was potential scanned from −0.2 V to +2.0 V (in 0.10 M aqueous NaCl) (FIG. 7(A)). This peak shift was also observed when the OM-NP conjugates were treated with various concentrations of $H_2O_2$ (FIG. 7(B)), but not with variations in the pH (pH 4 to pH 12), or upon irradiation with UV (254 nm for up to 75 min) (FIG. 8). These observations are consistent with the suggestion above that a positive potential on the gold surface induced a positive charge on the osmium atom, which ultimately led to an increase in the CO bond order and a blue-shift in the CO vibrations. In support of this, a density-functional theory (DFT) calculation performed on $Os_3(CO)_{10}(\mu\text{-Au})_2$ as the model showed that the Raman spectrum for the CO vibrations of the neutral species would shift to higher wavenumber in the charged species $[Os_3(CO)_{10}(\mu\text{-Au})_2]^+$ (FIG. 9).

Example 7: Computational Studies

The computational studies were carried out with DFT theory utilizing Becke's three parameter hybrid function (Becke, A. D., J. Chem. Phys. 1993, 98, 5648-5652), and the Perdew-Wang's gradient-corrected correlation function (B3PW91) (Perdew, J. P.; Burke, K.; Wang, Y. Phys. Rev. B 1996, 54, 16533-16539), together with the LanL2DZ (Los Alamos Effective Core Potential Double-ζ) basis set.

Vibrational frequencies were computed at 298.15 K and 1 atm pressure. All geometries were fully optimized with all real frequencies. All calculations were performed using the Gaussian 09 suite of programs.

Example 8: Potential-Dependent SERS Measurements

A 60 nm OM-NP-1 suspension was dropped onto a gold film, which was then left to dry under ambient conditions to form a nanoaggregate film. The film was washed with triply distilled water and then dried under a nitrogen ($N_2$) atmosphere. The potential of the electrochemical cell used for Raman spectral measurement was controlled by a potentiostat. All potentials are reported with respect to the silver/silver chloride (Ag/AgCl) electrode in a 0.1 M potassium chloride (KCl) solution.

Example 9: Fiber Preparation for SERS Detection

The HC-PCF (NKT Photonics) was cut into 7-centimeter lengths and both ends were cleaved using an optical fiber cleaver. One end of the fiber was plugged into the tip of a 0.3 mm syringe needle (BD PrecisionGlide) and the connection was sealed with a strong adhesive, ensuring that the liquid sample could be pumped into the fiber through a connected 1 ml tuberculin syringe (BD PrecisionGlide) for SERS measurement. The maximum volume of liquid in the side channel of this fiber segment was about 50 nL.

Example 10: $H_2O_2$ Detection in OSCC Cells

Figure 10:
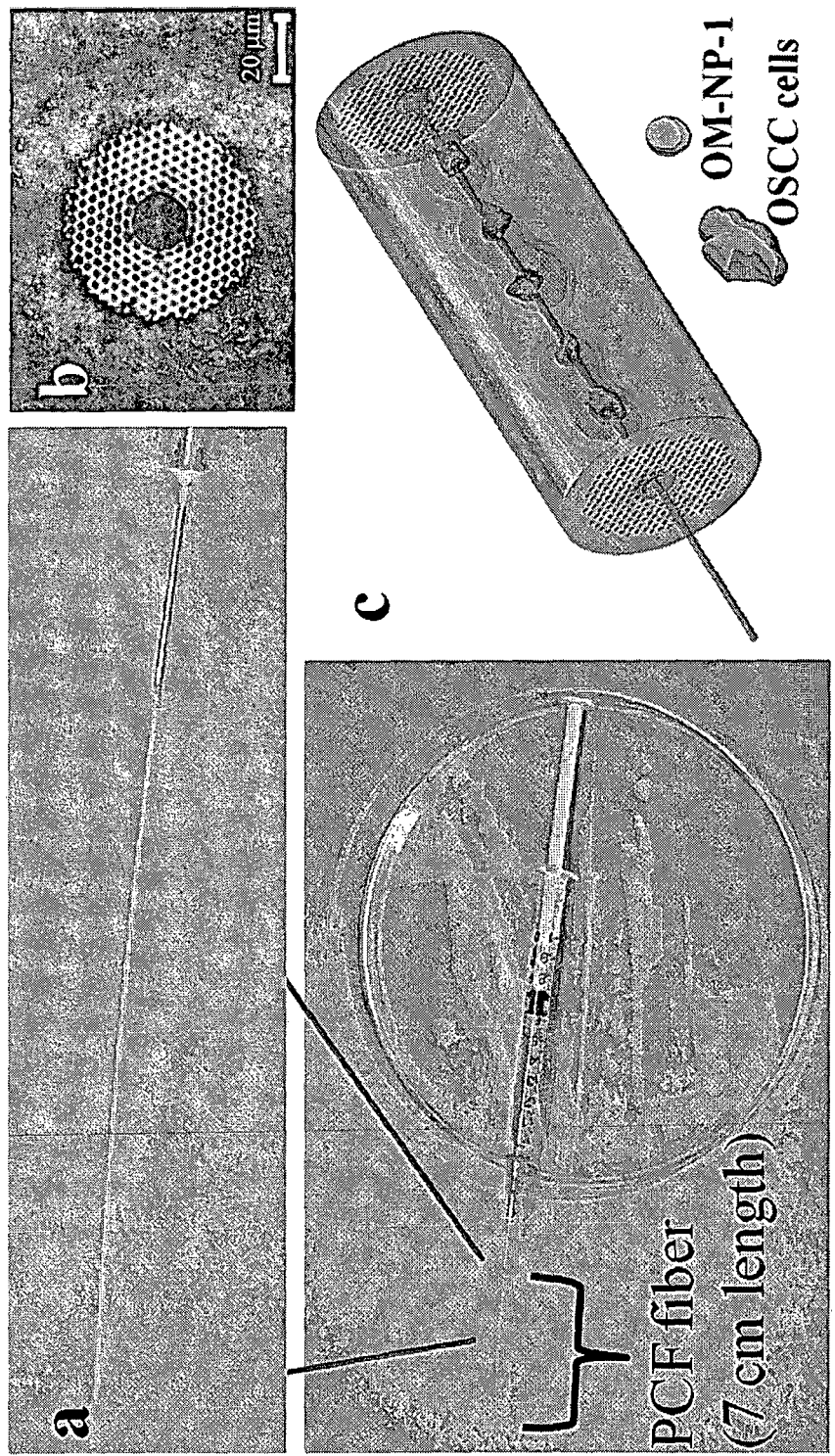
FIG. 10 depicts detection of $H_2O_2$ with OM-NP-1. (A) is a photo of a syringe connected to a hollow-core photonic crystal fibre (HC-PCF). An ultra low sample volume (about 50 nL) is required for SERS sensing. (B) is a microscope image of the cross-section of HC-PCF. (C) is a schematic diagram of HC-PCF as a SERS platform for ultra-lowvolume detection of $H_2O_2$ in cells sample. (D) shows SERS spectra of OM-NP-1 collected with ("+PCT") and without ("−PCF") the use of HC-PCF in the Raman shift range of 1900 cm$^{-1}$ to 2100 cm$^{-1}$. (E) shows SERS spectra of OSCC cells treated with OM-NP-1 and 20 μM of $H_2O_2$ vs control in the Raman shift range of 1900 cm$^{-1}$ to 2100 cm$^{-1}$. Scale bar in (B) denotes a length of 20 μm.
Figure 10:
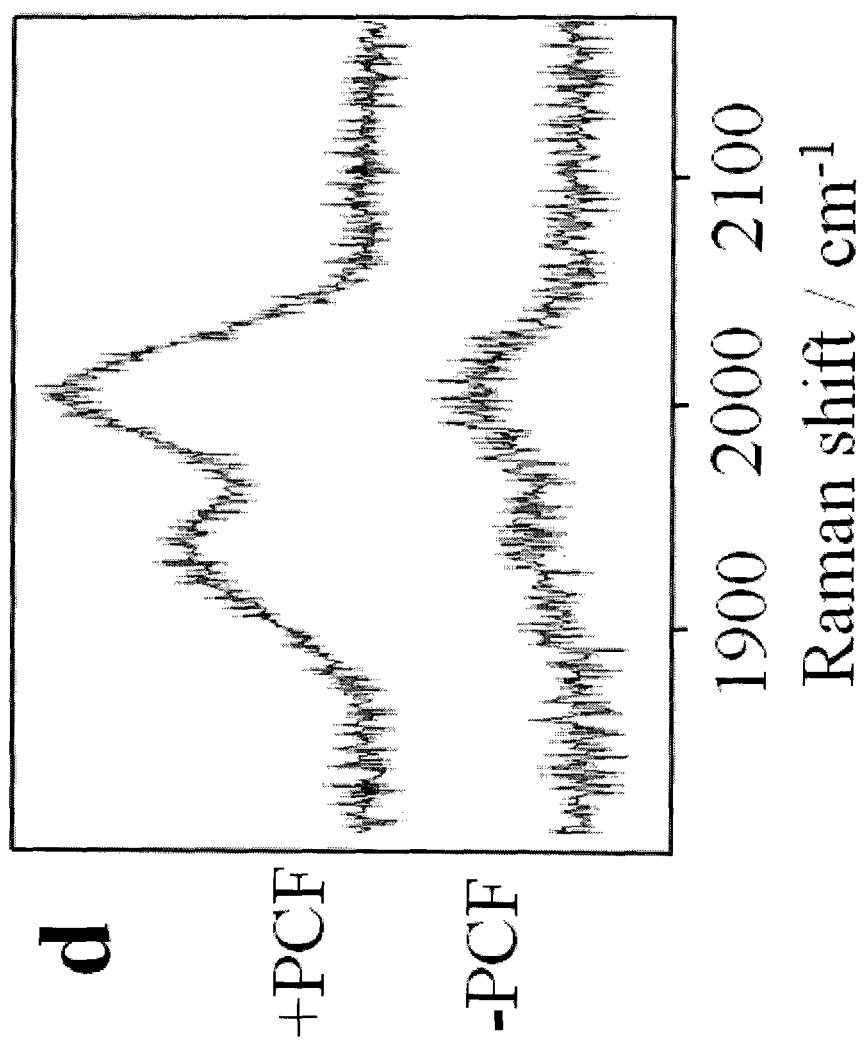
Figure 10:
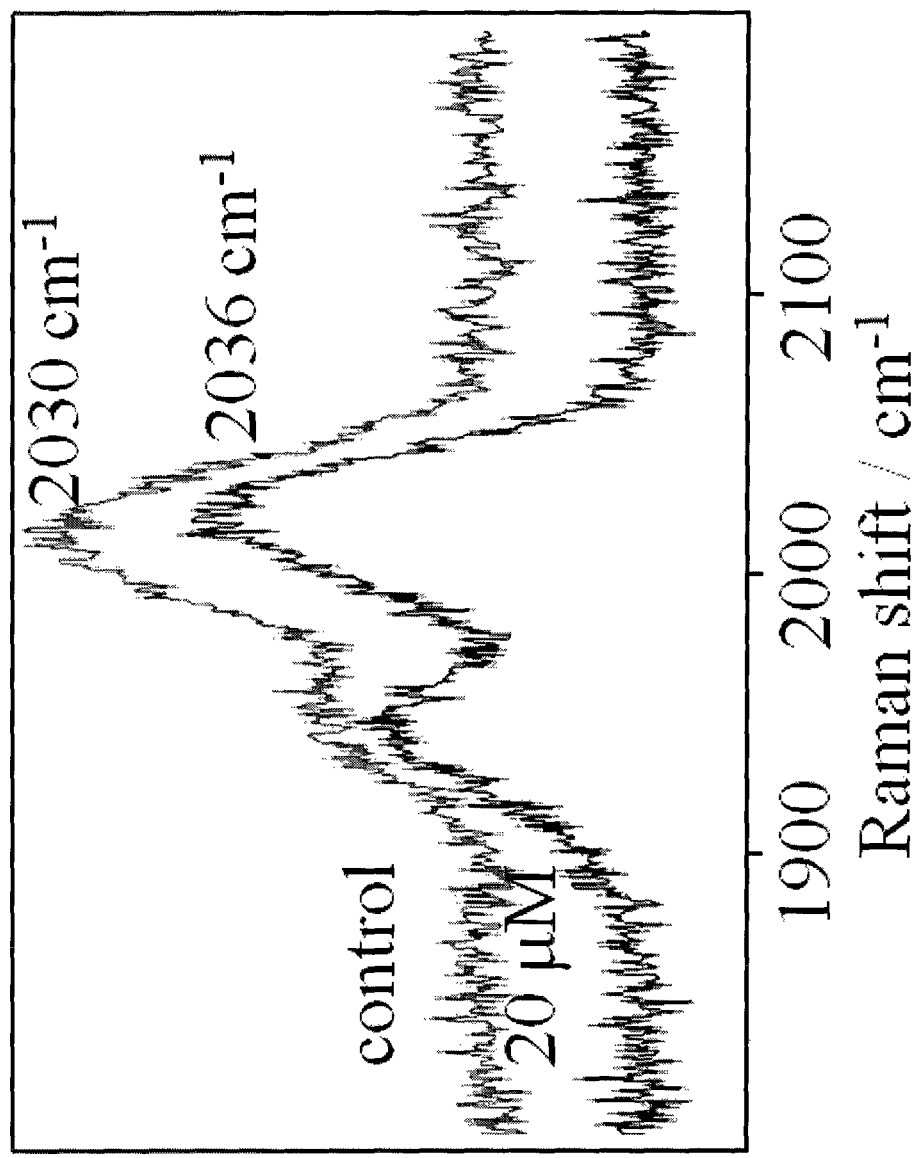

The OM-NP-1 conjugate was next applied to the detection of $H_2O_2$ within living cells at physiologically relevant concentrations (about 20 µM). For this, hollow core photonic crystal fiber (HC-PCF) detection, a high sensitivity and ultra-low-volume technique, was employed (FIGS. 10A and B).

Five thousand OSCC cells (ATCC Cell Lines) were seeded in a 96-well plate and then incubated for 24 h before the OM-NP-1 conjugate was introduced into each well and further incubated for another 24 h. The cells were then loaded onto a glass slide. Once the uptake of OM-NP-1 was confirmed by dark-field imaging, cell samples were then incubated with $H_2O_2$ (20 µM) for 30 min before transferring into the HC-PCF for SERS measurement.

Figure 11:
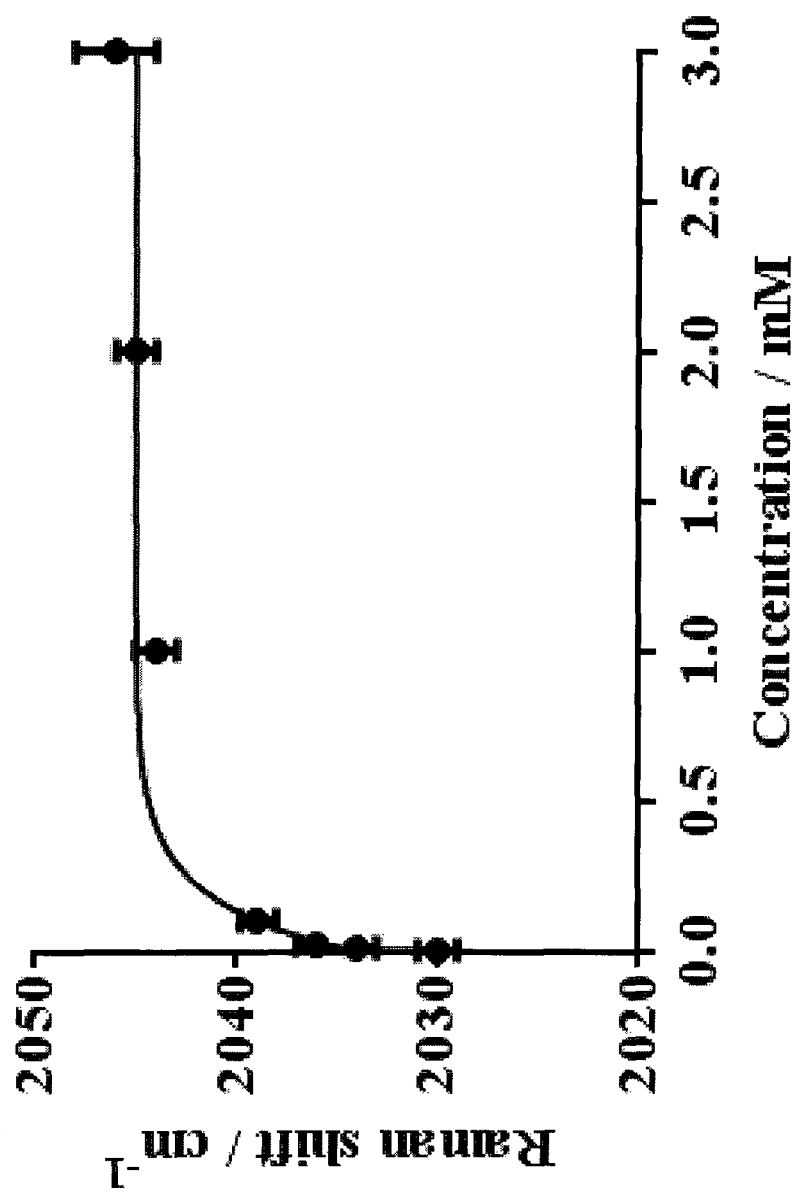
FIG. 11 is a graph showing CO stretching frequency versus concentration of $H_2O_2$.
Figure 12:
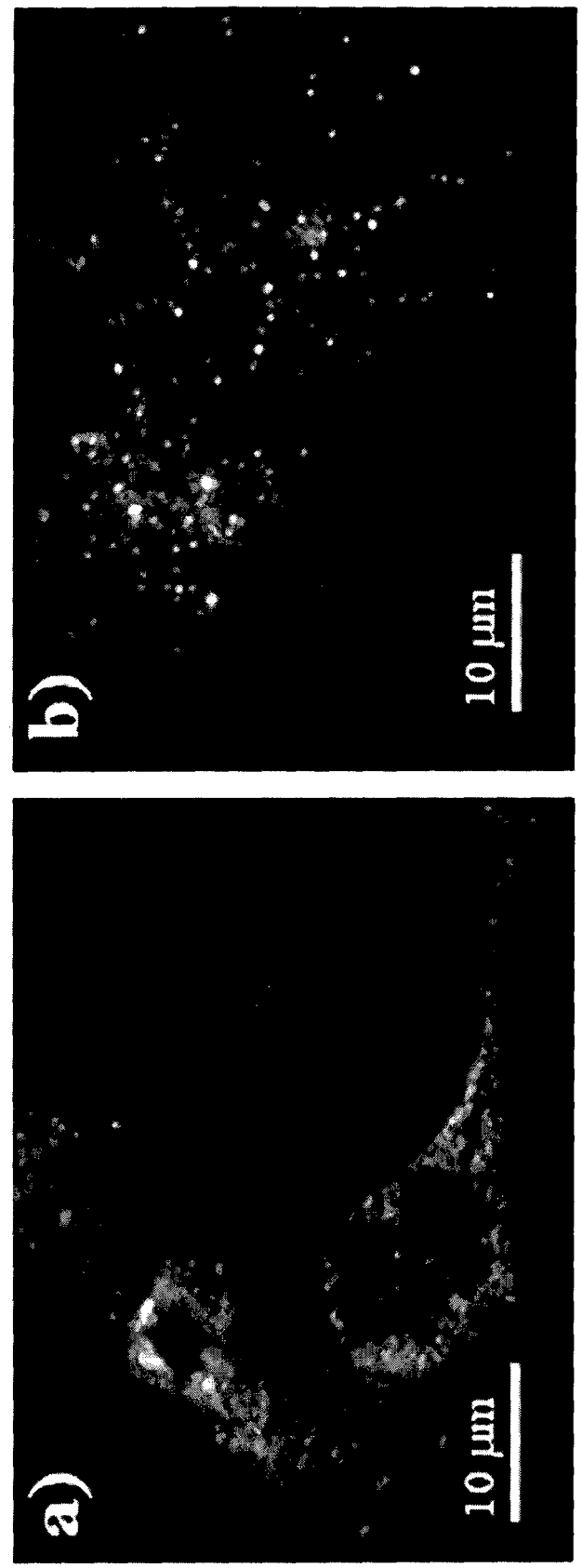
FIG. 12 shows dark field images of OSCC cells (A) before; and (B) after treatment with OM-NP-1. Scale bar in the figures denote a length of 10 μm.

In HC-PCF detection, the sample was pumped into a hollow core crystal fiber. The laser light was also transmitted through the fiber, allowing for stronger interaction with the sample as it was confined within the hollow core (FIG. 10C). This resulted in further enhancement of the signal (FIG. 10D), and a detection limit of 10 µM for $H_2O_2$ was achieved (FIG. 11). A low-volume sample (about 50 nL) of OSCC cells, which were incubated with OM-NP-1 and then with $H_2O_2$ before it was syringed into the HC-PCF, showed a shift in the SERS spectrum compared to an untreated control (FIG. 10E and FIG. 12). This clearly demonstrated that the use of the OM-NP-1 conjugate, in tandem with HC-PCF detection, may be used for the detection of $H_2O_2$ within cells.

Example 11: Detection of Thiol-Containing Biomolecules

The conjugate OM-NP-1 is prepared from the electronically unsaturated (46 electrons) cluster 1, which may be easily synthesized from available starting materials.

Freshly prepared solutions of 1 in ethanol (200 µL, 1 mM) were mixed with aqueous solutions of biomolecules (200

μL) and incubated for 1 min. The gold NP solution (100 μL) was added to each prior to Raman spectral measurements.

Figure 13:
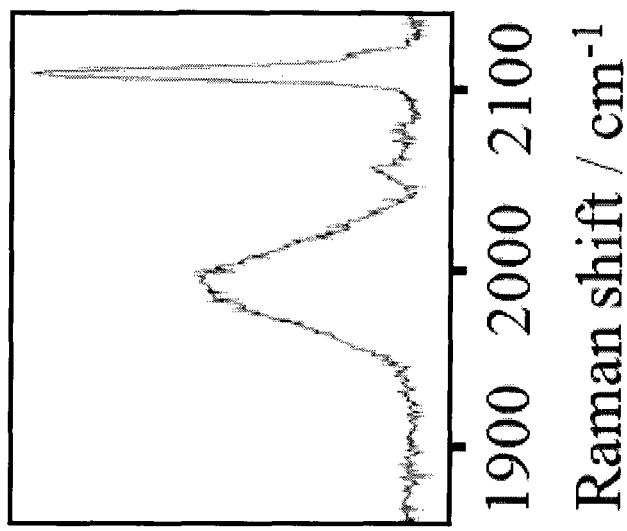
FIG. 13 depicts detection of thiol with the precursor of OM-NP-1. (A) shows a reaction scheme for cluster 1 with a thiol. (B) shows Raman spectrum (CO vibrations) of the resulting μ,κS-thiolate bridged cluster in the Raman shift range of 1900 cm$^{-1}$ to 2100 cm$^{-1}$.
Figure 13:
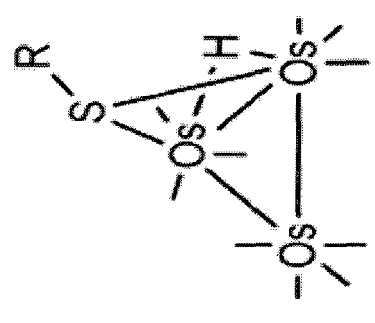
Figure 13:
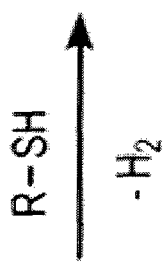
Figure 13:
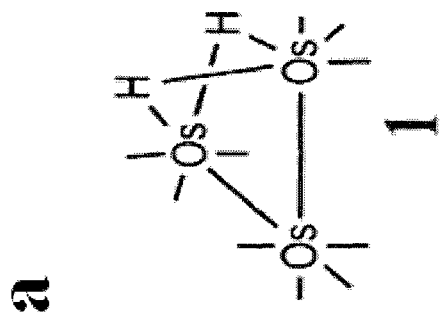
Figure 14:
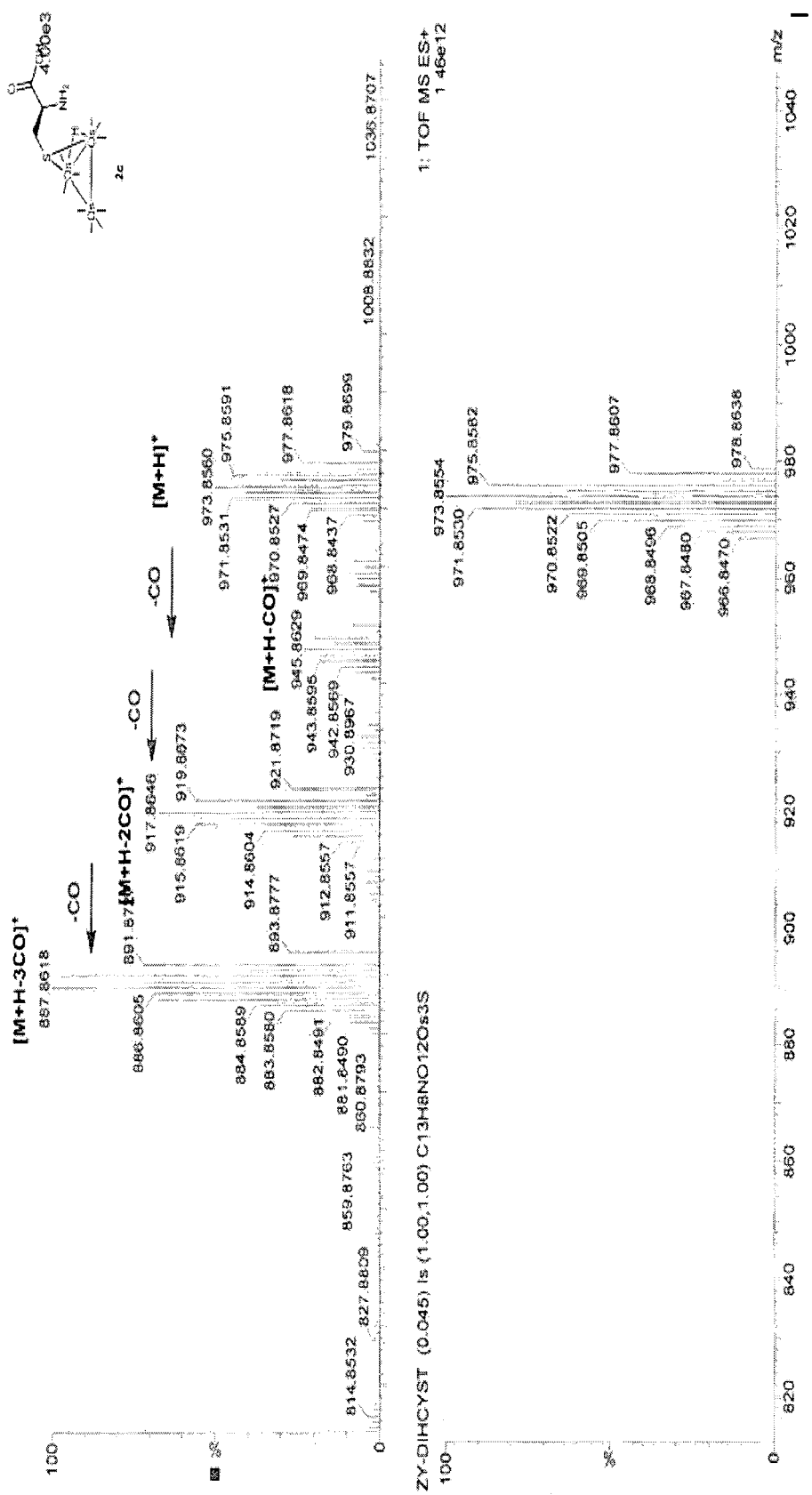
FIG. 14 shows HR ESI-MS for the reaction of $Os_3(CO)_{10}(\mu-H)_2$ with cysteine (top) with calculated isotopic pattern (bottom). Y-axis denote % from 0 to 100, and x-axis denote m/z in the range of 820 to 1040, with increment of 20 per labeled interval.
Figure 15:
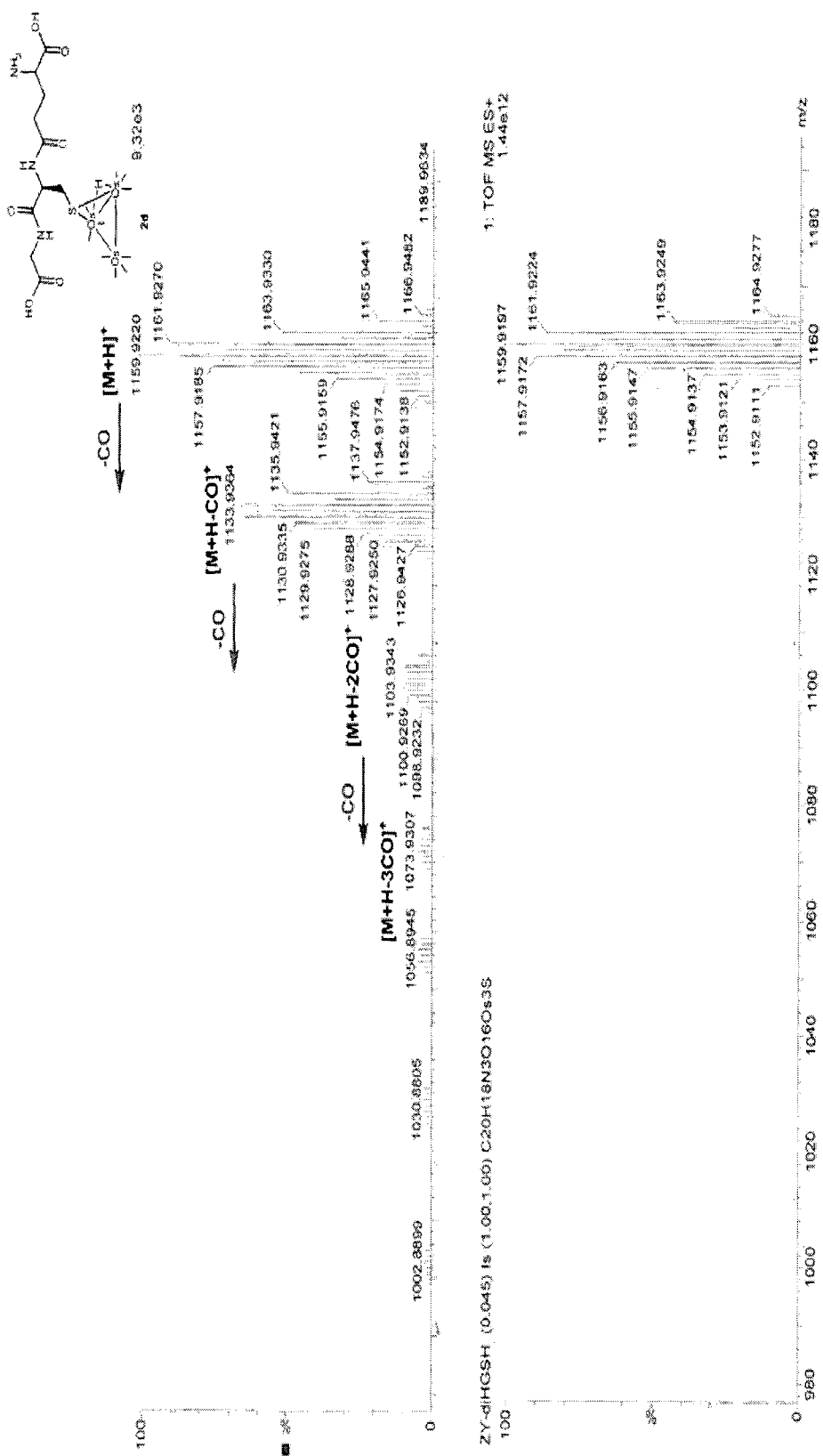
FIG. 15 shows HRMS-ESI for the reaction of $Os_3(CO)_{10}(\mu-H)_2$ with GSH (top) with calculated isotopic pattern (bottom). Y-axis denote % from 0 to 100, and x-axis denote m/z in the range of 980 to 1180, with increment of 20 per labeled interval.

The heavier transition metal carbonyls have a high affinity towards the thiol (SH) functionality, more so than towards, say, the carboxylic acid (COOH) and amine ($NH_2$) functionalities. Cluster 1 is such an example; it exhibits higher reactivity towards thiols (—SH) over other functional groups to form the μ,κS-thiolate bridged cluster (48 electrons) (FIG. 13, FIG. 14, and FIG. 15). The formation of such a thiolate-bridged cluster results in changes in the spectrum for the CO stretching vibrations, and is characterised by a very intense peak at 2111 $cm^{-1}$. The frequency shift on the reaction of 1 with thiols may therefore form the basis of a detection system for biologically important thiols.

Thiol-containing biomolecules are ubiquitous in nature and are vital in many biological processes. They are important for metabolic regulation, the maintenance of cellular redox potential, and also the activity of many sulfhydryl enzymes. There is also increasing evidence for thiols as disease biomarkers. For instance, elevated levels of cysteine are related to a number of health disorders, including motor neurone, Alzheimer's and Parkinson's disease. Deficiency in glutathione (GSH), a low molecular weight molecule, is a sign of oxidative stress which can lead to ageing and the onset of many diseases. Detection methods for thiols are thus of interest but, to-date, there has been no report of a SERS-based probe. Part of the reason is that functional groups used to react with thiols, such as maleimide, do not have high Raman cross-sections and their Raman signals overlap with those from other biomolecules.

Example 12: Detection of Thiol and $H_2O_2$ in Clinical Urine Samples

Figure 16:
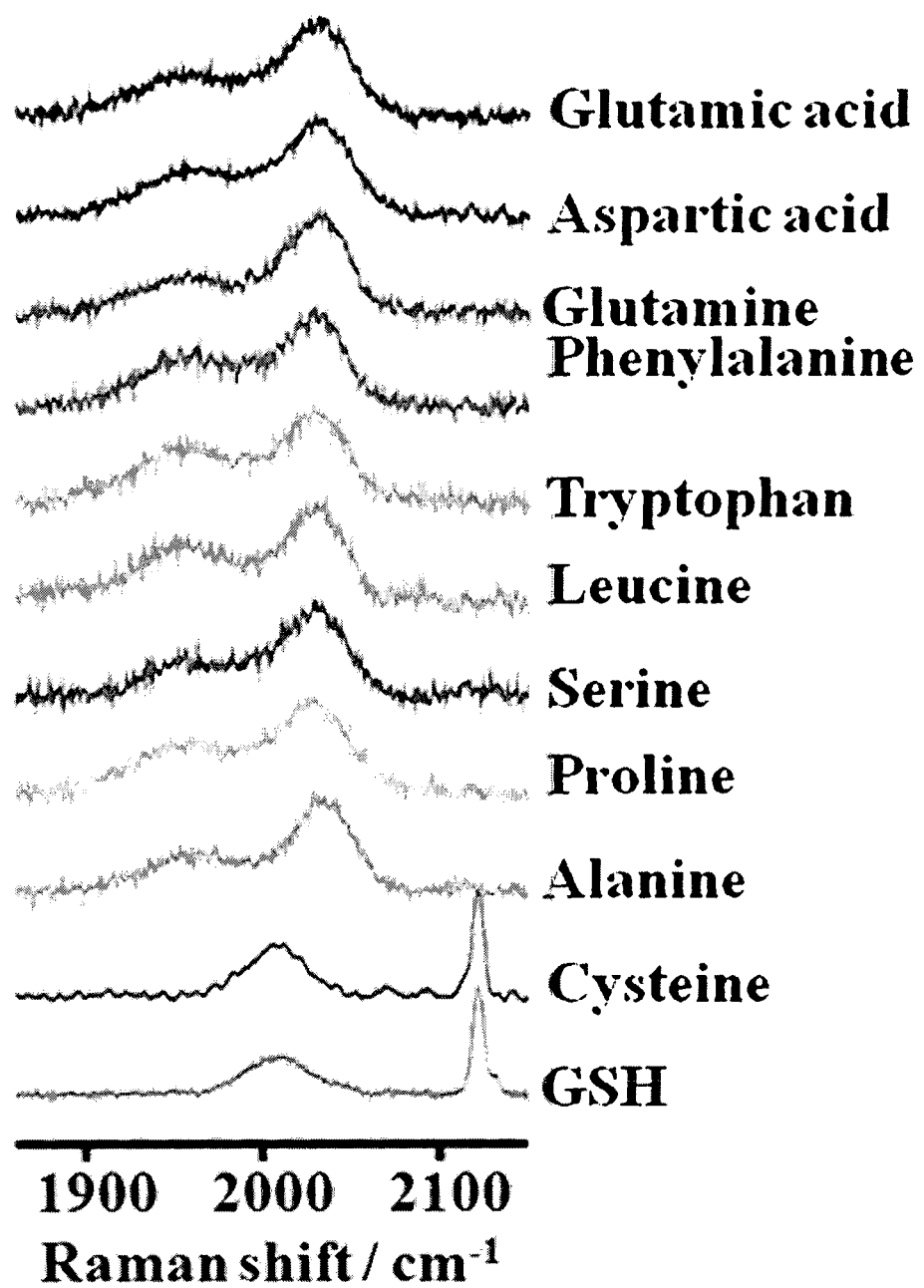
FIG. 16 shows SERS spectra of 1 treated with various amino acids of glutamic acid, aspartic acid, glutamine, phenylalanine, tryptophan, leucine, serine, proline, alanine, cysteine, and GSH in the Raman shift range of 1900 cm$^{-1}$ to 2100 cm$^{-1}$.
Figure 17:
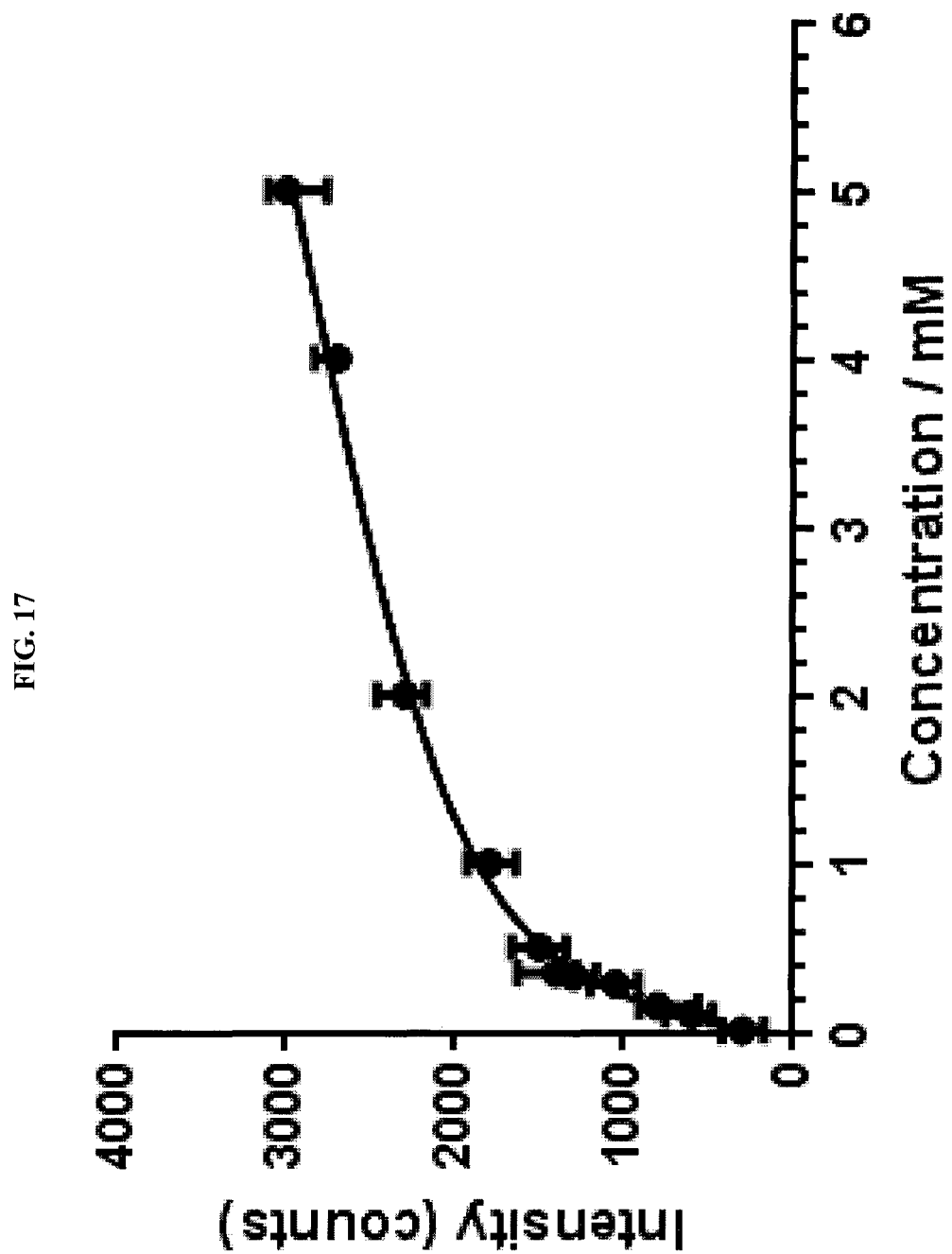
FIG. 17 shows plot of $v_{CO}$ Raman intensity versus concentration of GSH.
Figure 18:
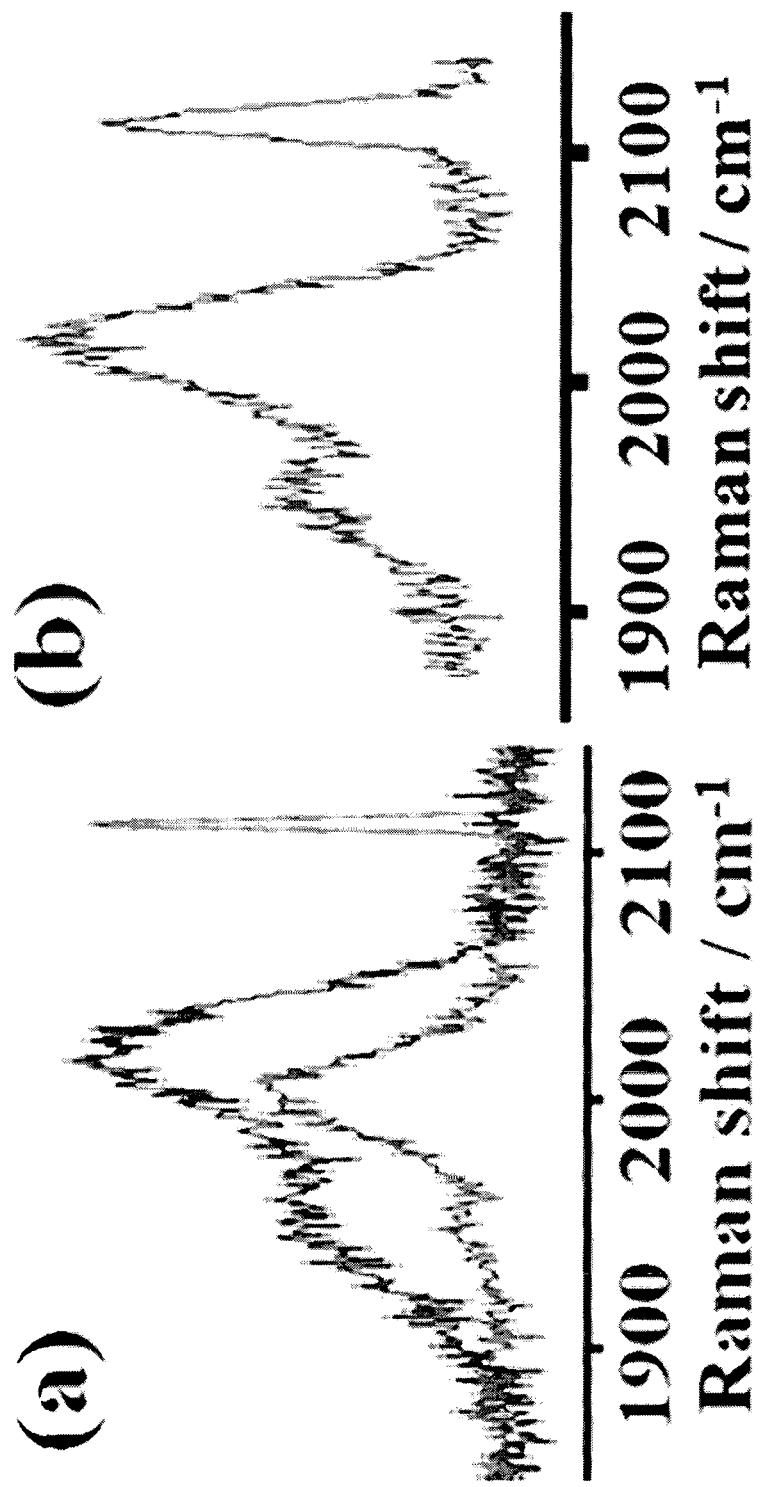
FIG. 18 shows (A) overlap of SERS spectra for OM-NP-1 and (GSH)thiolate-bridged carbonyl cluster; and (B) SERS spectrum showing the formation of OM-NP-1 and (GSH) thiolate-bridged carbonyl cluster by 1. The latter spectrum was obtained from the reaction of GSH (100 μL, 1 mM) with a freshly prepared solution of 1 in ethanol (100 μL, 2 mM), incubated for 1 min, followed by incubation with gold NP solution (100 μL, 2.6×10$^{11}$ particles/mL, BBInternational UK) for another min, then transferred into the HC-PCF for SERS measurement.

Treatment of 1 with GSH and various amino acids show that the peak at 2111 $cm^{-1}$ was not observed with thiol-free amino acids (FIG. 16). A peak assignable to OM-NP-1 was observed instead, indicating its formation from unreacted 1 and gold NPs during the SERS measurement. With GSH, the intensity of the 2111 $cm^{-1}$ peak increased with concentration, with the limit of detection estimated at 20 μM (FIG. 17). That the peaks assignable to OM-NP-1 and the thiolate-bridged cluster do not overlap (FIG. 18) suggests that two distinct spectroscopic handles for dual detection within one system have been obtained.

Figure 19:
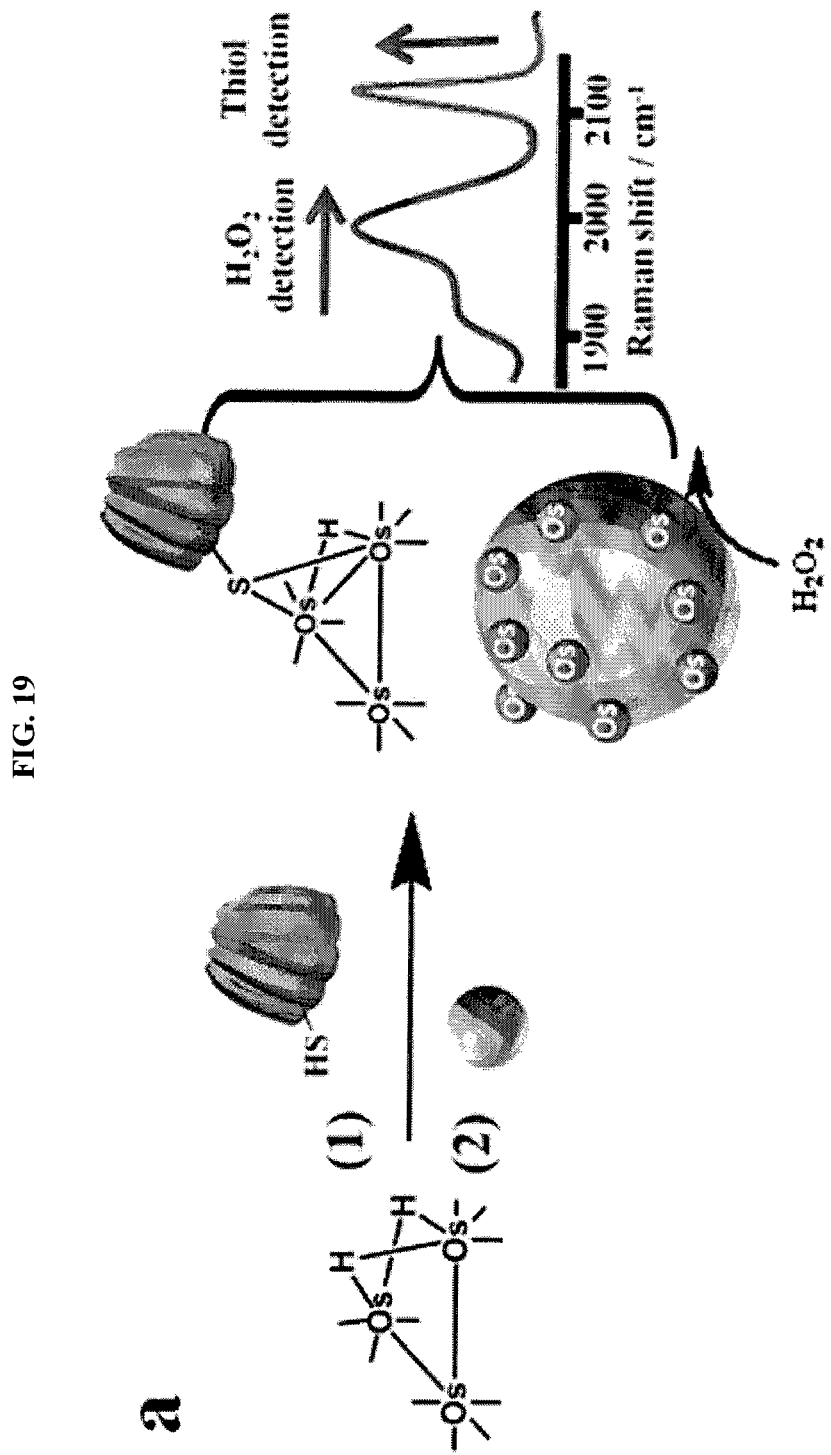
FIG. 19 depicts dual detection of $H_2O_2$ and thiol, where (A) is a schematic diagram for the detection of $H_2O_2$ and thiol molecules, with detection in a PCF fiber; and (B) is a graph showing SERS response for different concentrations of thiol and $H_2O_2$.
Figure 19:
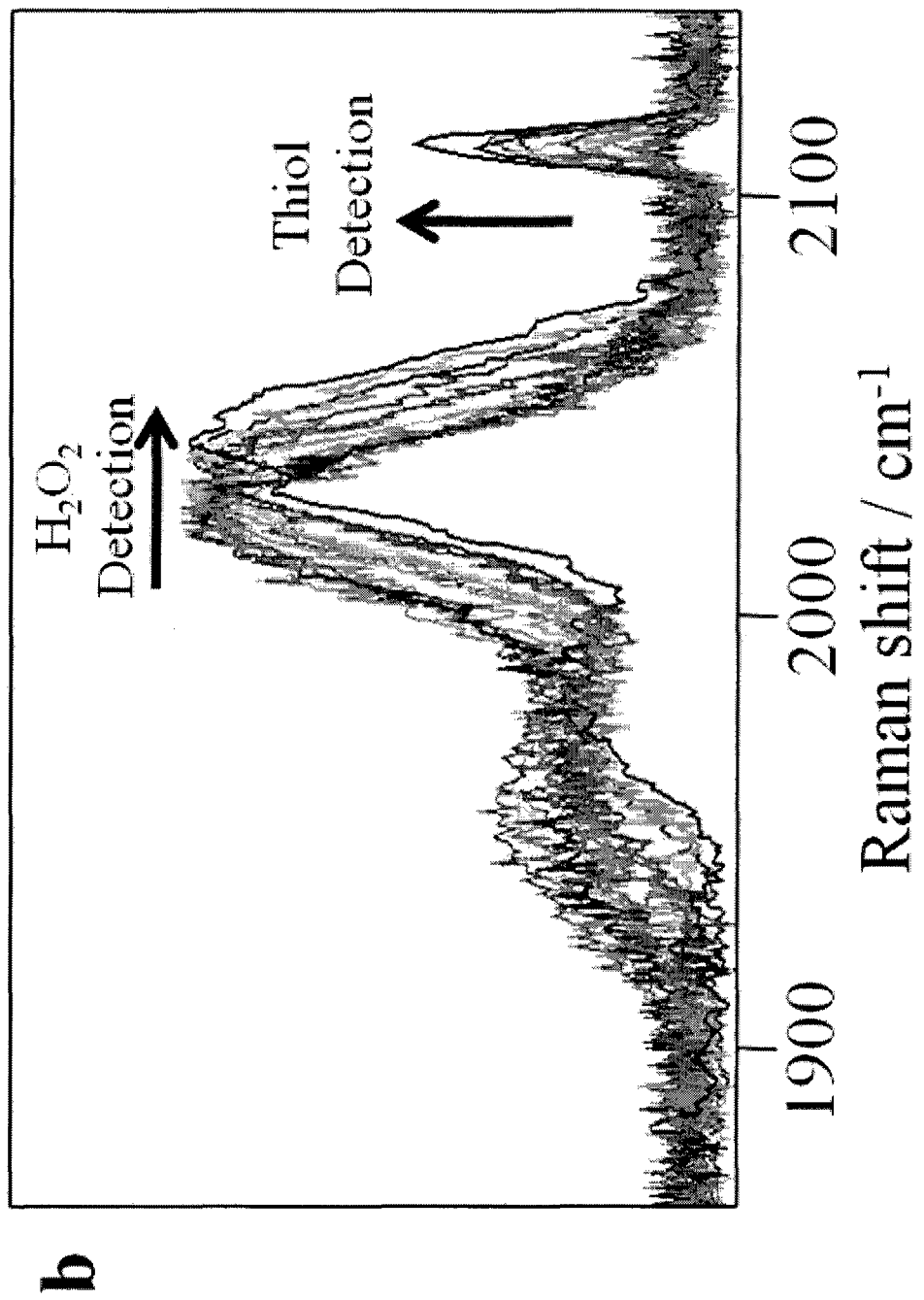

A novel procedure for the dual detection of $H_2O_2$ and thiol using one system can thus be envisaged (FIG. 19A). The sequential addition of a thiol sample to a solution of 1, followed by the addition of gold NPs, allows the instantaneous reaction of the thiol with 1 to form the thiolate-bridged cluster. Excess 1 then reacts with the gold NP, forming OM-NP-1 for $H_2O_2$ detection (FIG. 19B).

Samples used for the study were from clinical specimens, stored at −20° C. Specimens were used in accordance with procedures approved by the local ethics committee (CIRB Re 2011/558/C), and informed consents were given by all patients. The urine (20 μL) was mixed with freshly prepared solutions of 1 in ethanol (100 μL, 2 mM) and incubated for 1 min. After incubation, the gold NP solution (100 μL, 2.6×10¹¹ particles/mL, BBInternational UK) was added and the mixture incubated for 1 min, and then transferred into the HC-PCF for SERS measurement.

Deviations in the amount of urinary thiol excreted can be a sign of health disorders. For instance, elevated levels of urinary excretion of thiols have been associated with inflammation, myocardial infarction, and autoimmune diseases like rheumatoid arthritis. On the other hand, patients with proteinuria showed significantly decreased levels of urinary protein thiols compared to healthy controls. Similarly, the level of $H_2O_2$ excreted in urine can reflect metabolic and oxidation events in body, making its measurement a valuable tool for the assessment of metabolic events such as oxidative stress. Thus the urine analysis above revealed that thiol levels in the cancer subjects were generally lower than the non-cancer subjects. On the other hand, they show higher $H_2O_2$ levels. The lower levels of thiol may correlate with an increased level of oxidation processes in the cancer subjects as it is known that disease conditions can result in the oxidative modification of thiol molecules, leading to protein degradation and damage. Bladder cancer subjects have been reported to have a higher oxidative stress index. $H_2O_2$ in urine is a potential biomarker of oxidative stress, which plays a key role in cancer and protein oxidation.

Figure 20:
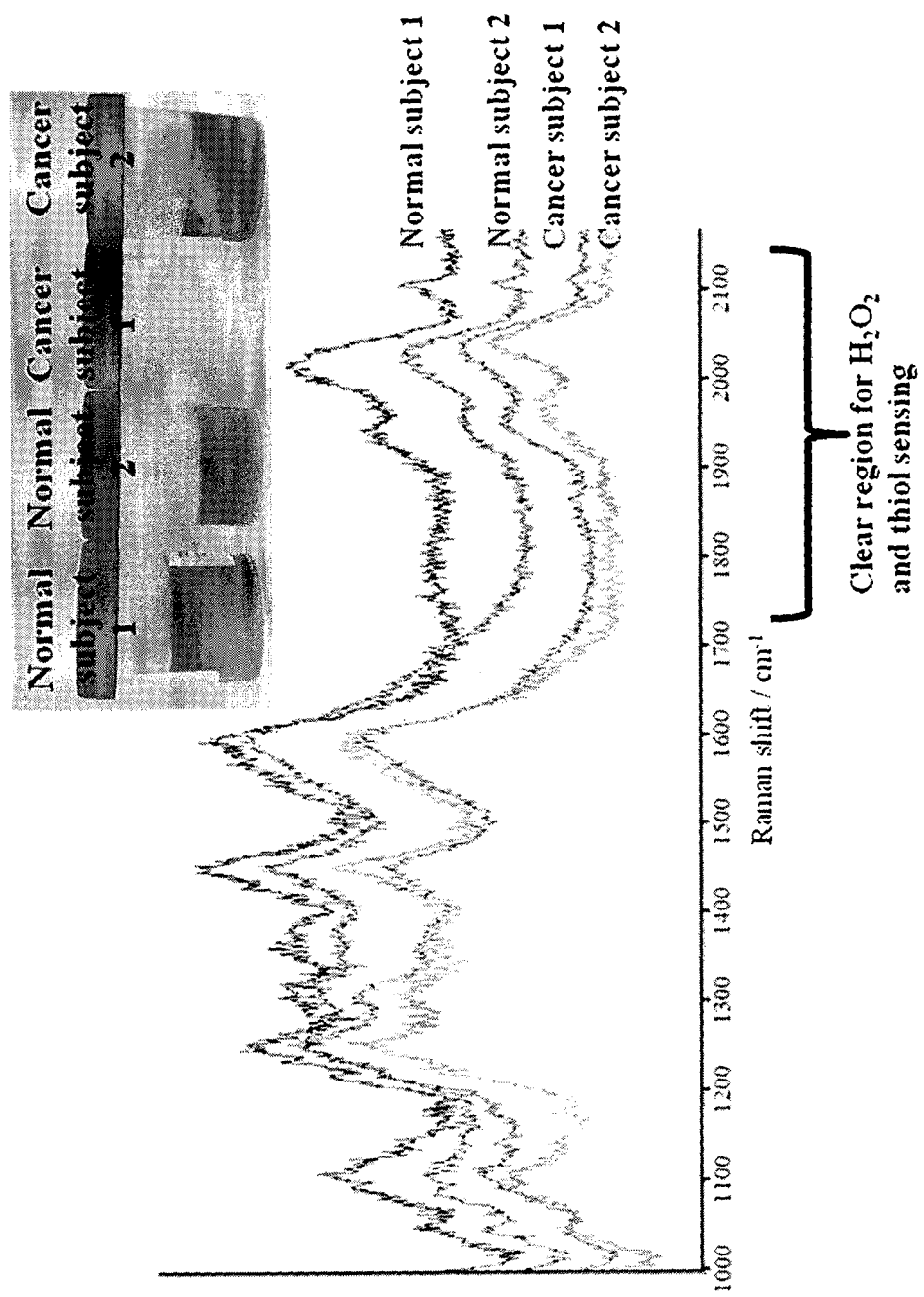
FIG. 20 shows photographs and SERS spectra of urine samples of Normal subject 1, Normal subject 2, Cancer subject 1, and Cancer subject 2 incubated with gold NPs and cluster 1 in the Raman shift range of 1000 cm$^{-1}$ to 2100 cm$^{-1}$.

The configuration described above has been used to determine the concentration of thiols and $H_2O_2$ in human urine samples (FIG. 20). Samples from two normal subjects (NS) sand two patients with bladder cancer (CS) were analysed, and the values obtained were in good agreement with those determined by two separate commercial kits (TABLE 1). The good distinction between non-cancer and bladder cancer urinary levels suggests that it may be possible to establish valid diagnostic cutoff thresholds for urinary biochemicals.

TABLE 1

Thiol and $H_2O_2$ concentrations for urine specimens

| Cytoscopy Findings | Thiol concentration/μM | | $H_2O_2$ concentration/μM | |
|---|---|---|---|---|
| | Our method | Thiol kit | Our method | $H_2O_2$ kit |
| NS 1 Normal | 151 | 133 | 18 | 15.3 |
| NS 2 Normal | 96.6 | 84 | 22 | 18.8 |
| CS 1 Cancer | 53 | 46 | 45 | 39 |
| CS 2 Cancer | 46 | 37 | 62 | 54 |

Example 13: Detection of $H_2O_2$ in Clinical Urine Samples Using Commercial Kit The $H_2O_2$ concentration in urine was determined using a commercial kit (Cayman Chemicals). The urine sample was diluted 1:50 with water before assaying. The urine sample (20 μL) was placed into a 96-well plate, catalase (10 μL) added, followed by the $H_2O_2$ detector (200 μL), and then incubated for 60 min before reading the plate.

Example 14: Detection of Thiols in Clinical Urine Samples Using Commercial Kit The thiol concentration in urine was determined by a commercial kit (Cayman Chemicals). The urine sample was diluted 1:50 with water before assaying. The urine sample (50 μL) was placed into a 96-well plate. Thiol fluorometric detector (50 μL) was then added, and the sample incubated for 5 min before reading the plate.

Example 15: Detection of Glucose

Blood glucose monitoring and urine glucose monitoring are the two primary methods used by the person with diabetes to monitor their diabetes control. Urine glucose monitoring is not a substitute for blood glucose monitoring, but rather an alternative or complement which can provide very valuable information where blood glucose monitoring is not accessible, affordable, or desired.

The sensitivity of the OM-NP-1 conjugate to $H_2O_2$ concentration suggested that it may also be used in the determination of glucose via an enzymatic assay.

Glucose oxidase (GOx) is an enzyme that converts glucose to gluconic acid and $H_2O_2$. It is, however, only active at acidic pH. The good pH stability of the OM-NP-1 conjugate suggests that it may be an ideal probe for GOx activity under its optimal acidic condition.

To demonstrate the potential practicality of our sensor system, we determined glucose in urine samples after spiking them with standard glucose solutions. The glucose samples with serial dilutions were incubated with GOx (1 mg/mL, sigmal-aldrich) for 1 h. The solution (10 μL) was then incubated with freshly prepared OM constructs (20 μL) for 10 min and the SERS spectra were collected.

Figure 21:
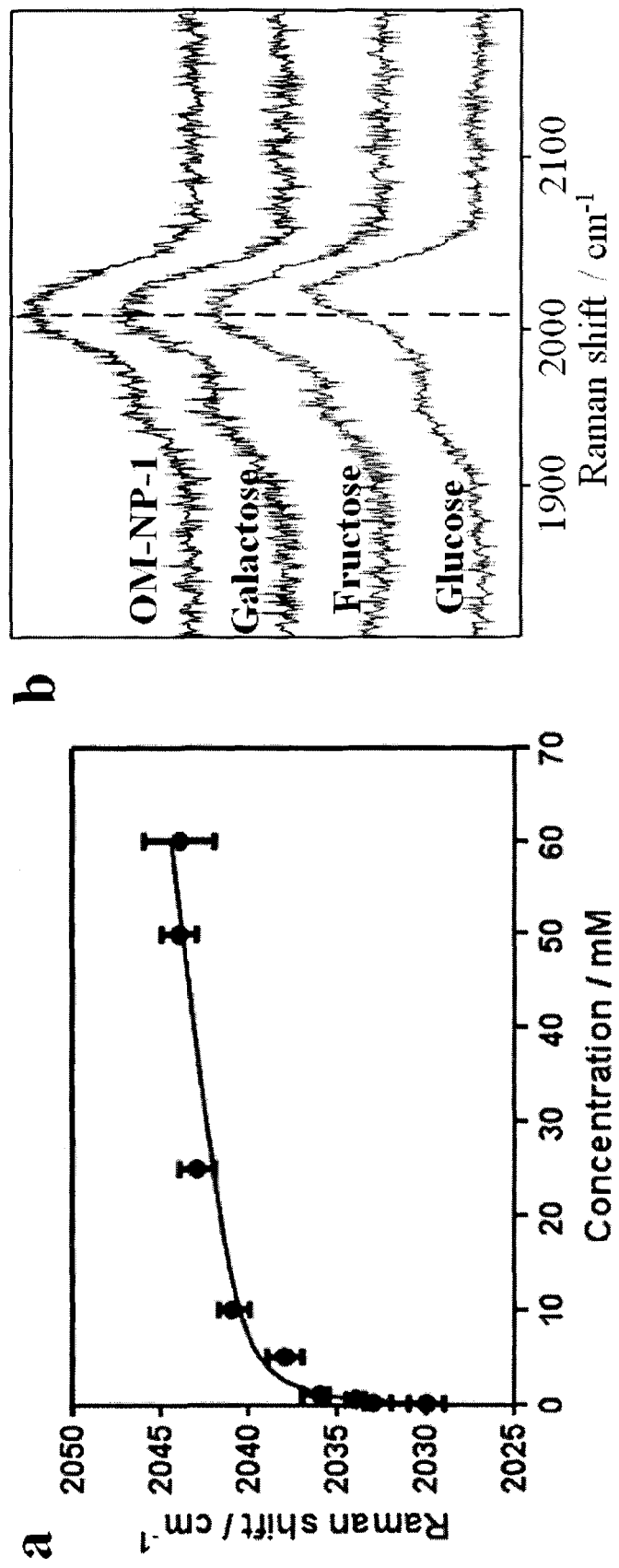
FIG. 21 depicts detection of glucose with OM-NP conjugates, where (A) is a plot of CO stretching frequency versus different concentrations of glucose; and (B) is a graph showing SERS response of OM-NP-1 with glucose, fructose and galactose.
Figure 22:
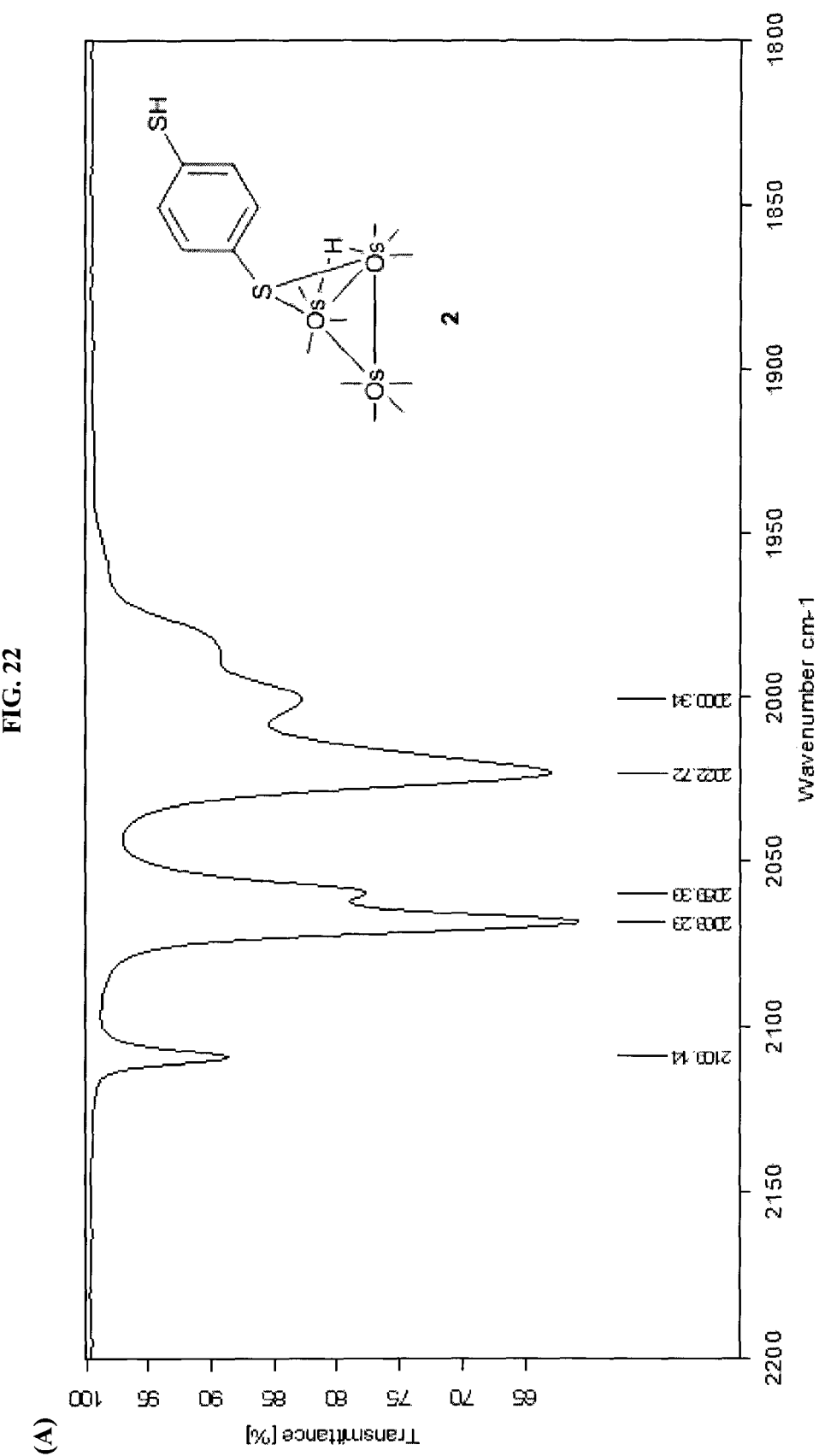
FIG. 22 depicts spectroscopic characterisation for 2, where (A) is solution IR spectrum ($CH_2Cl_2$); (B) is $^1$H NMR spectrum; (C) $^{13}$C{$^1$H} NMR spectrum. In (A), y-axis denotes transmittance (%) with labels from 65 to 100 at increments of 5 per interval; x-axis denotes wavenumber cm$^{-1}$ in the range of 1800 to 2200. Peaks at 2109.14, 2088.23, 2069.33, 2022.72, and 2000.34 are indicated. In (B) and (C), y-axis represents intensity (arbitrary unit/a.u.), while x-axis represents magnetic field strength (scale is in parts per million (ppm)). Peaks for (B) 7.17, 3.45, 1.54, 0.00, −17.04; (C) 180.69, 180.19, 176.09, 171.97, 172.16, 169.34, 142.54, 132.95, 132.31, 129.02, 77.54, 0.29.
Figure 22:
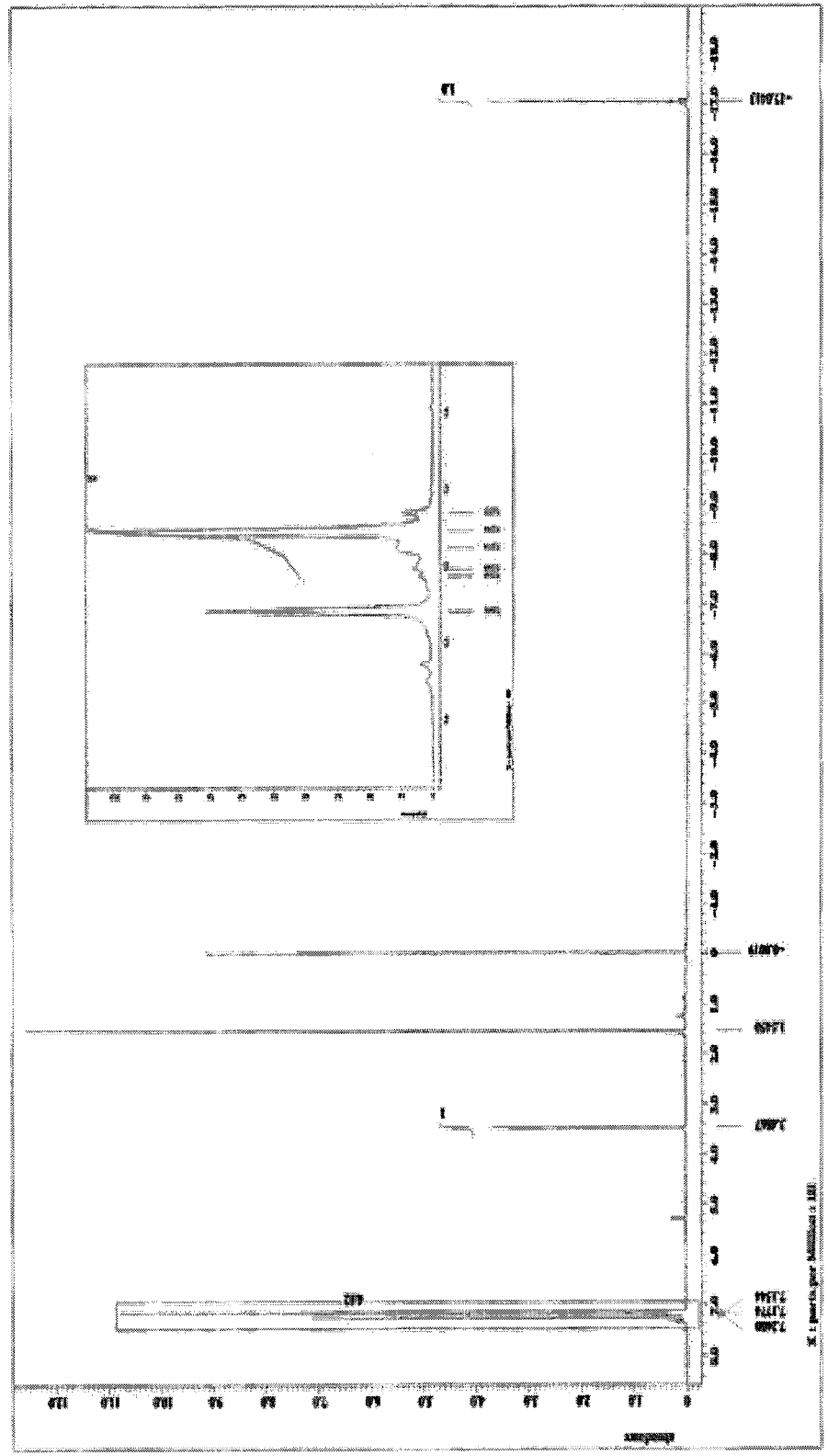
Figure 22:
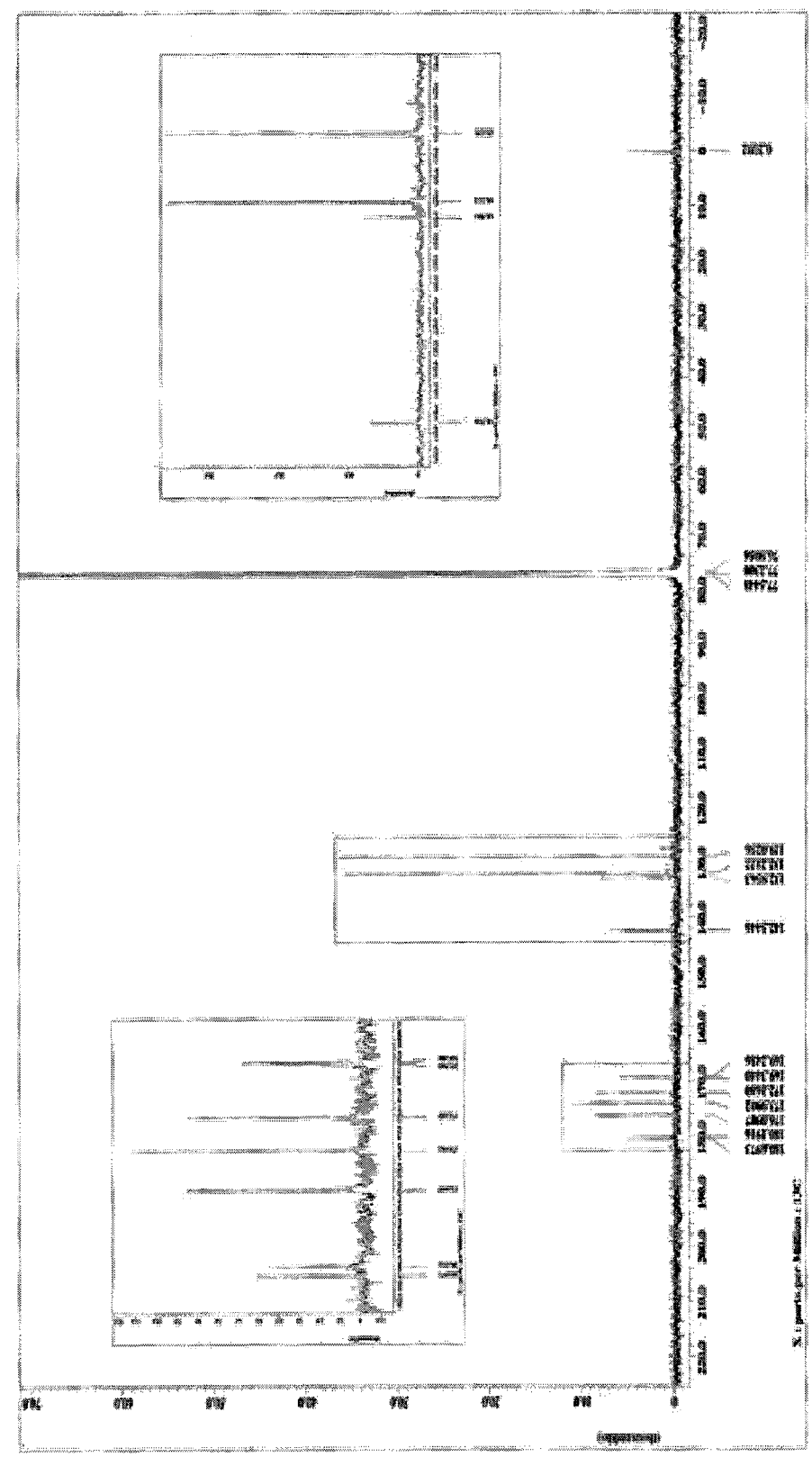
Figure 23:
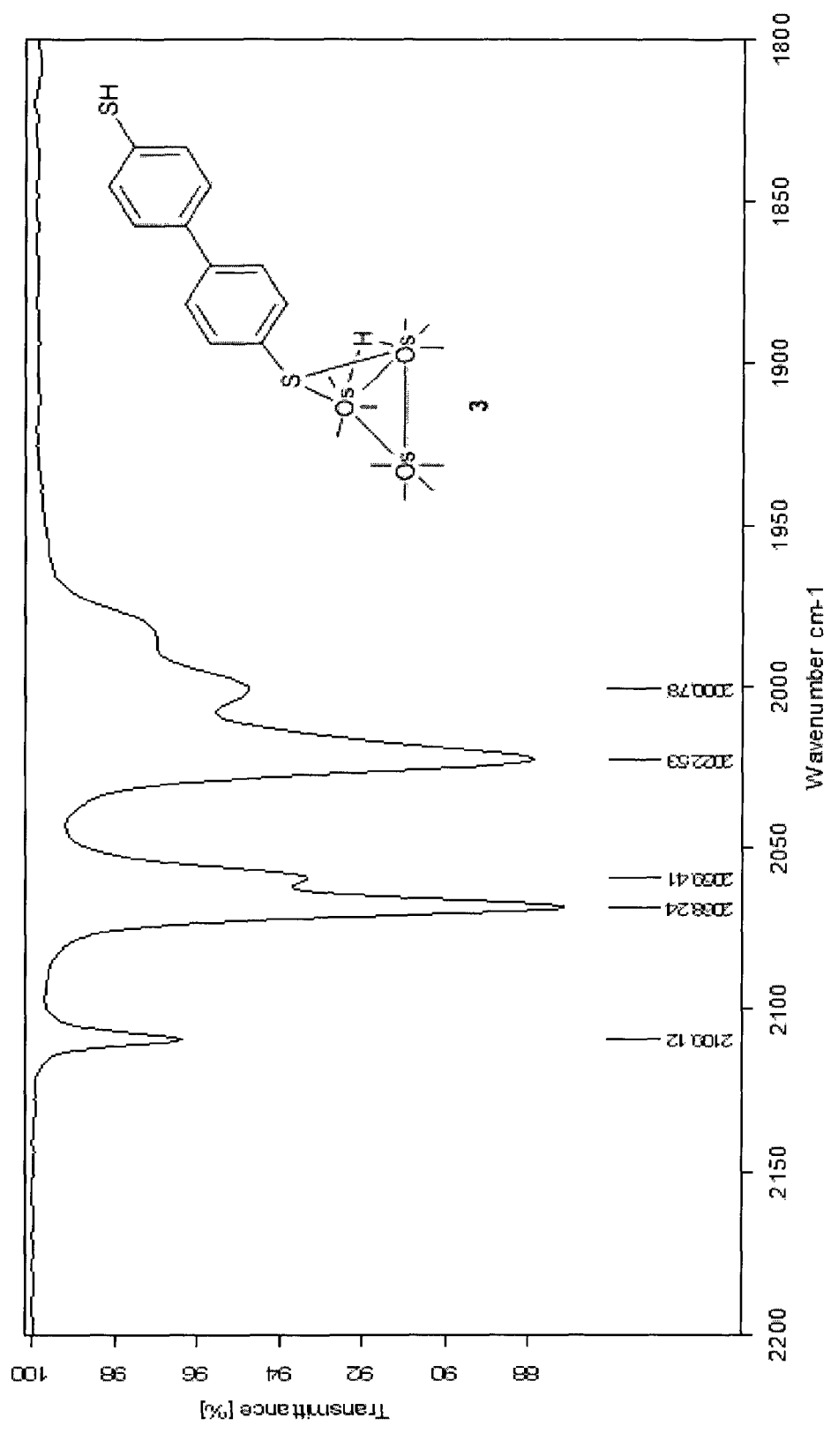
FIG. 23 depicts spectroscopic characterisation for 3, where (A) is solution IR spectrum ($CH_2Cl_2$); (B) is $^1$H NMR spectrum; (C) $^{13}$C{$^1$H} NMR spectrum. In (A), y-axis denotes transmittance (%) with labels from 88 to 100 at increments of 2 per interval; x-axis denotes wavenumber cm$^{-1}$ in the range of 1800 to 2200. Peaks at 2109.12, 2088.24, 2069.41, 2022.53, and 2000.78 are indicated. In (B) and (C), y-axis represents intensity (arbitrary unit/a.u.); while x-axis represents the magnetic field strength (scale is in parts per million (ppm)). Peaks for (B) 7.45, 7.32, 7.36, 3.49, 1.54, 0.00; (C) 180.74, 180.25, 176.15, 174.01, 172.19, 169.41, 169.34, 141.33, 141.18, 137.30, 132.11, 129.93, 127.81, 126.85, 77.55, 77.23, 76.99, 0.29.
Figure 23:
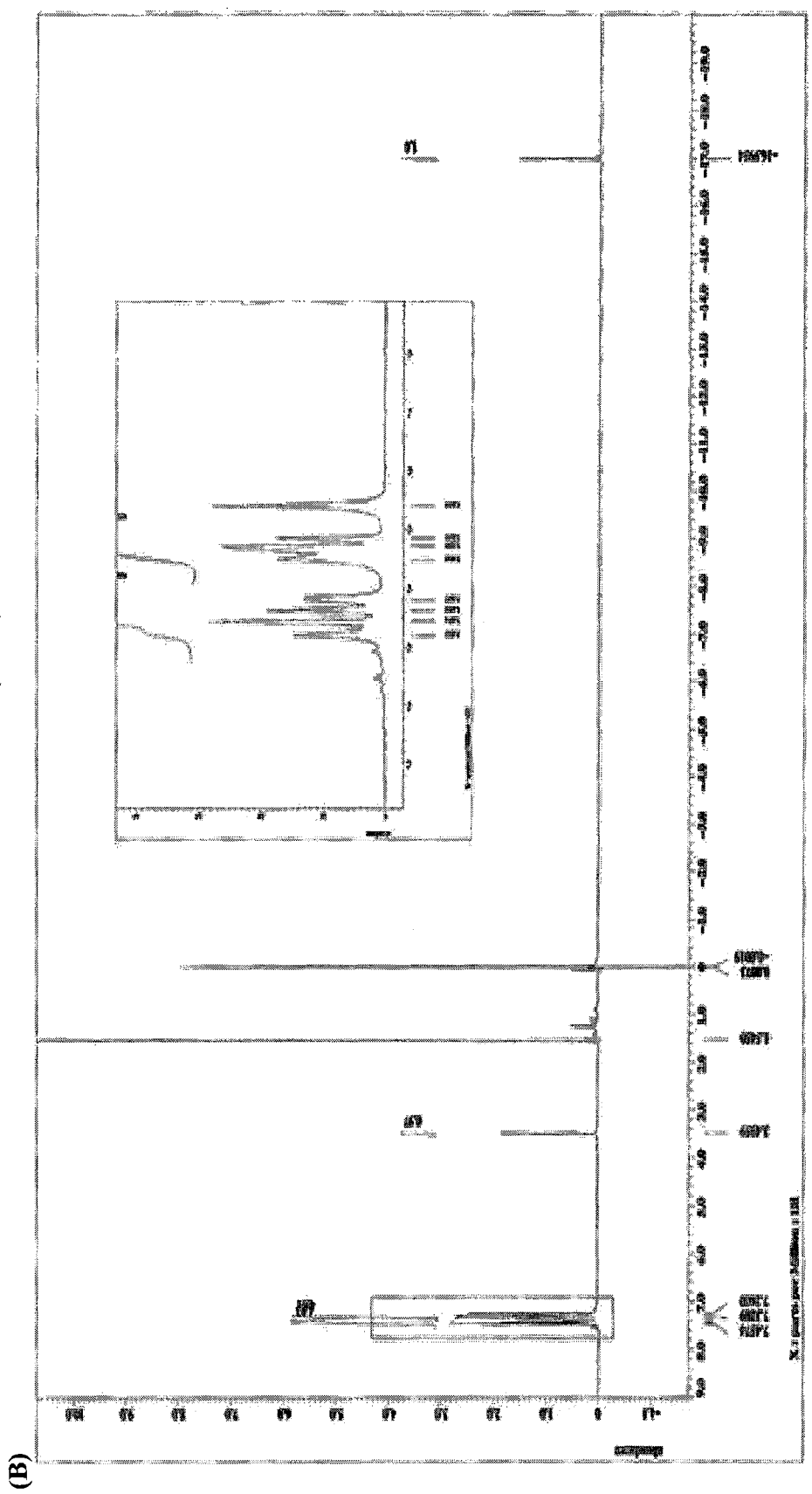
Figure 23:
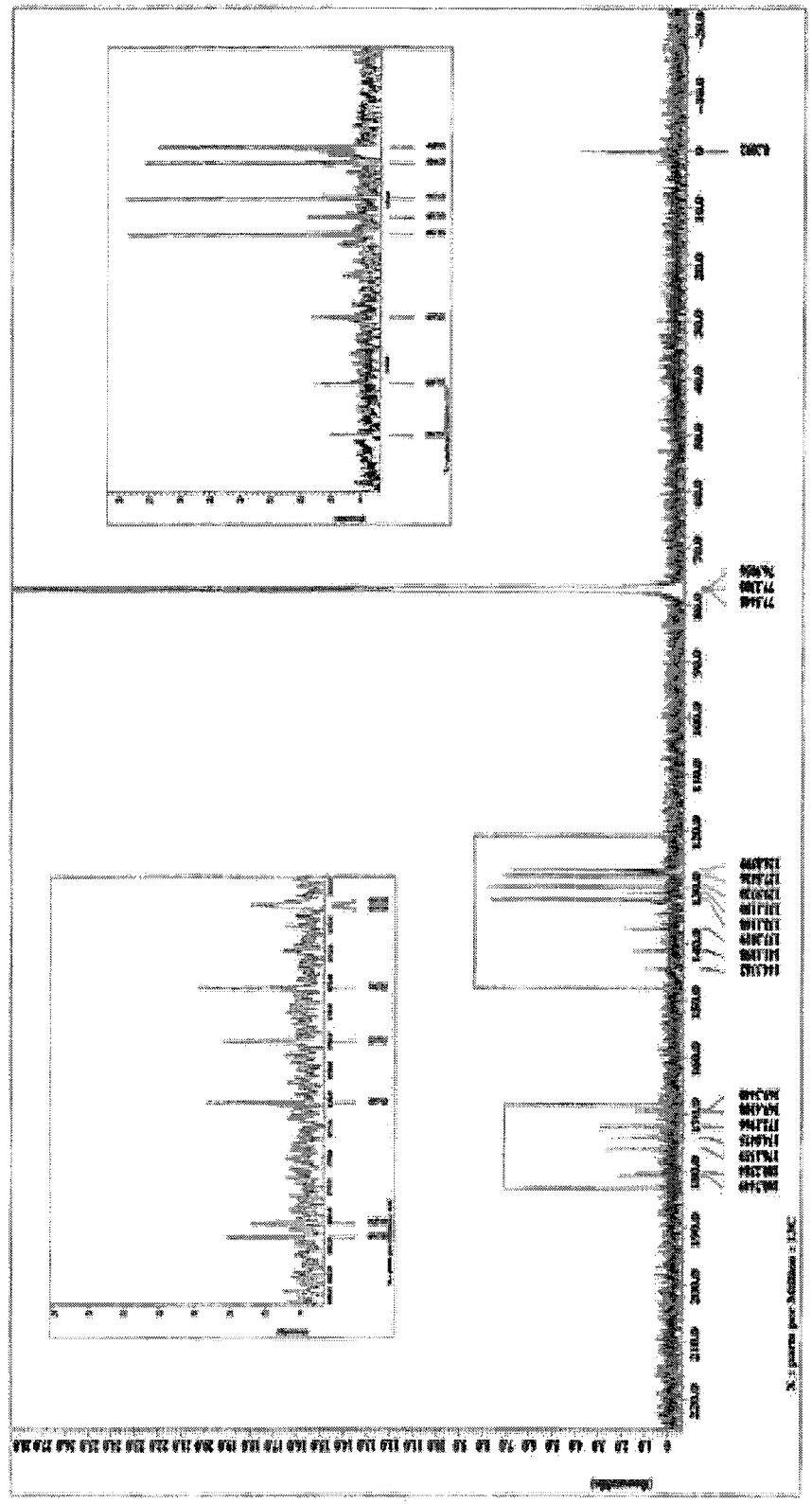

A plot of the SERS peak against the concentration of glucose over the 0.1 to 60 mM range, which covered the physiological range, showed that the detection limit was about 0.2 mM (FIG. 21A). Control experiments using fructose and galactose (5 mM) showed no observable peak shifts (FIG. 21B), thus demonstrating selectivity for glucose. The low volume and concentration limits suggest that this method may be applied to the detection of, for example, glucose level in tear; this has been reported to be in the 0.1 mM to 0.6 mM range, the normal rate of secretion of tears being about 1 μL/min and can be lower in the morning, after prolonged lid closure.

Concentration of glucose in the urine samples was determined to be 3.7 mM, in good agreement with that (4.0 mM) amount of glucose added into urine. The effectively determination of glucose in urine samples has implied that this OM-NP constructs glucose detection method has potential in clinical diagnosis.

Experiments for detection of glucose in clinical urine sample were carried out. In the experiments, human urine sample was provided by Dr Weber Lau in Singapore General Hospital. Urine sample was added a known amount of glucose. The final urine solution was agitated upon GOx incubation for 1 h. The solution (10 μL) was then incubated with OM constructs and SERS measurement was taken after 10 min.

A mechanism is put forward based on the changes of surface potential of gold NPs by $H_2O_2$. Compared with other glucose detection reported in the literature, this OM-NP constructs assay exhibits several advantages. First, the whole detection system is based on simply mixing OM-NP constructs and solution. Second, the OM-NP constructs were able to sensitively detect glucose over a wide concentration range, which may be used for the detection of physiological levels of glucose in bio-fluid using CO stretching vibrations without interference from biomolecules.

Given these unparalleled advantages, it is envisaged that this OM-NP constructs assay will be a promising tool for clinical diagnose of glucose in near future.

In conclusion, it has been shown herein that change in surface potential of a gold nanoparticle that is induced by the presence of $H_2O_2$ may be utilized for its detection. This has been demonstrated through a frequency shift in the CO vibrations of a water-dispersible OM-NP conjugate. The idea has been extended to detection of $H_2O_2$ in cells, and to enzymatic glucose detection, at extremely low sample volume and concentration, by coupling it with HC-PCF for the SERS detection. The OM-NP conjugate may sensitively detect both $H_2O_2$ and glucose over a wide range of concentrations in biofluids because it leverages on the fact that the CO stretching vibrations are free from interference by the vibrational modes of biomolecules. It has also been demonstrated herein that the known chemistry of the precursor compound used in the synthesis of the OM-NP conjugate may be utilized in a novel protocol that allows for the simultaneous SERS detection of $H_2O_2$ and thiol biomolecules. The inventors believe that this is the first time that such a SERS-based dual-functionalities detection method has been demonstrated. The positive results from studies conducted using clinical urine samples demonstrate its feasibility for clinical use.

The proposed label-free detection system based on OM-NP constructs has the following novelties. Firstly, OM-NP is easy to manufacture even at laboratory scale that may reduce manufacturing time, and costs. Secondly, low amounts of reagents such as OM-NP (such as 2 μL to 10 μL, generally about 5 μL) and analyte (5 μL or more) are required. 50 mL of OM-NP, for example, may be used to perform up to 10,000 assays. There is only a short incubation time requirement as SERS changes instantly or within seconds such as 10 seconds or less. There is high sensitivity since the carbonyl signal is in a biologically silent region (1800 cm$^{-1}$ to 2200 cm$^{-1}$) where most endogenous molecules in biofluids show no Raman scattering. It is thus able to analyze the CO peak without interference from absorption of biomolecules. The method may be translated easily for use in a chip-based sensor, or a microfluidic device, by immobilization OM-NP on surface of a chip. This sensing strategy may be used to determine many other analytes, such as uric acid, lactate, glutamate, and cholesterol, when performed in conjunction with suitable enzymes, as well as for complex samples or biofluids, since the sample does not require purification prior to measurement.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting one or more analytes comprising hydrogen peroxide using surface enhanced Raman spectroscopy (SERS), the method comprising
   a) providing a SERS-active substrate having at least one metal carbonyl cluster compound attached thereon;
   b) contacting the one or more analytes with the SERS-active substrate; and
   c) detecting changes in surface enhanced Raman signal from the at least one metal carbonyl cluster compound as an indication of the presence of the one or more analytes comprising hydrogen peroxide.

2. The method according to claim 1, wherein the at least one metal carbonyl cluster compound has general formula (I)

$$M_3(CO)_xL_{12-x} \qquad (I)$$

wherein

M at each occurrence denotes a metal selected from Group 6 to Group 11 of the Periodic Table of Elements;
x is an integer from 10 to 12;
and each L is independently selected from the group consisting of —H and —S—$(C_6H_4)_n$—SH,
wherein n is an integer from 1 to 3.

3. The method according to claim 2, wherein M is independently selected from the group consisting of Fe, Ru, and Os.

4. The method according to claim 2, wherein M is Os.

5. The method according to claim 2, wherein x is 10.

6. The method according to claim 2, wherein n is 1 or 2.

7. The method according to claim 1, wherein the at least one metal carbonyl cluster compound is selected from the group consisting of $Os_3(CO)_{10}(\mu\text{-}H)_2$, $Os_3(CO)_{10}(\mu\text{-}H)(\mu\text{-}SC_6H_4\text{-}p\text{-}SH)$, $Os_3(CO)_{10}(\mu\text{-}H)(\mu\text{-}SC_6H_4\text{—}C_6H_4\text{-}p\text{-}SH)$, and combinations thereof.

8. The method according to claim 1, wherein the SERS-active substrate comprises gold nanoparticles.

9. The method according to claim 1, wherein the SERS-active substrate comprises gold nanoparticles having a mean diameter in the range of about 40 nm to about 100 nm.

10. The method according to claim 1, wherein contacting the one or more analytes with the SERS-active substrate is carried out in the presence of a suitable enzyme.

11. The method according to claim 10, wherein the one or more analytes comprising hydrogen peroxide aregenerated by reaction with the enzyme.

12. The method according to claim 11, wherein the one or more analytes comprising hydrogen peroxide generated by reaction with the enzyme are selected from the group consisting of glucose, uric acid, lactate, glutamate, and cholesterol.

13. The method according to claim 11, wherein the one or more analytes comprising hydrogen peroxide generated by reaction with the enzyme comprise glucose.

14. The method according to claim 13, wherein the enzyme comprises glucose oxidase.

15. The method according to claim 1, wherein the SERS-active substrate having at least one metal carbonyl cluster compound attached thereon is formed by providing at least one unbound metal carbonyl cluster compound, allowing the one or more analytes to react with the at least one unbound metal carbonyl cluster compound, and attaching the resulting at least one metal carbonyl cluster compound to the SERS-active substrate.

16. The method according to claim 15, wherein the one or more analytes comprises a thiol group.

17. The method according to claim 1, wherein detecting changes in surface enhanced Raman signal from the at least one metal carbonyl cluster compound comprises at least one of (i) detecting changes in pattern and/or intensity of SERS signal in the region of 1800 $cm^{-1}$ to 2200 $cm^{-1}$, and (ii) detecting peak shifts in surface enhanced Raman spectrum from the at least one metal carbonyl cluster compound as an indication of the presence of the one or more analytes.

18. The method according to claim 1, wherein the hydrogen peroxide is generated in one or more living cells.

19. The method according to claim 1, wherein the one or more analytes comprising hydrogen peroxide is detected in a body fluid comprising the one or more analytes.

20. The method according to claim 19, wherein the body fluid is selected from the group consisting of plasma, serum, blood, lymph, liquor and urine.

\* \* \* \* \*

UNITED STATES PATENT AND TRADEMARK OFFICE
CERTIFICATE OF CORRECTION

| | |
|---|---|
| PATENT NO. | : 9,915,670 B2 |
| APPLICATION NO. | : 15/022362 |
| DATED | : March 13, 2018 |
| INVENTOR(S) | : Olivo et al. |

Page 1 of 1

It is certified that error appears in the above-identified patent and that said Letters Patent is hereby corrected as shown below:

In the Claims

<u>Column 21,</u>
Line 17, "aregenerated" should read --are generated--.

Signed and Sealed this
Twenty-fourth Day of July, 2018

Andrei Iancu
*Director of the United States Patent and Trademark Office*